(12) United States Patent
Reed et al.

(10) Patent No.: US 11,826,046 B2
(45) Date of Patent: Nov. 28, 2023

(54) SURGICAL STAPLER HAVING A POWERED HANDLE

(71) Applicant: Applied Medical Resources Corporation, Rancho Santa Margarita, CA (US)

(72) Inventors: Christina N. Reed, Trabuco Canyon, CA (US); Matthew M. Becerra, Lake Forest, CA (US); Andrew J. McCarthy, Trabuco Canyon, CA (US); Scott Zimmerman, Lancaster, CA (US); Joshua M. Schober, Temecula, CA (US); Steven E. Decker, Anaheim, CA (US); Kevin Hudson, Rancho Santa Margarita, CA (US); Andy Pham, Rancho Santa Margarita, CA (US)

(73) Assignee: Applied Medical Resources Corporation, Rancho Santa Margarita, CA (US)

( * ) Notice: Subject to any disclaimer, the term of this patent is extended or adjusted under 35 U.S.C. 154(b) by 73 days.

(21) Appl. No.: 17/591,356

(22) Filed: Feb. 2, 2022

(65) Prior Publication Data
US 2022/0151612 A1    May 19, 2022

Related U.S. Application Data

(60) Continuation of application No. 16/821,830, filed on Mar. 17, 2020, now Pat. No. 11,272,934, which is a
(Continued)

(51) Int. Cl.
*H02J 7/00* (2006.01)
*A61B 17/072* (2006.01)
(Continued)

(52) U.S. Cl.
CPC .... *A61B 17/07207* (2013.01); *A61B 17/2909* (2013.01); *H02J 7/00* (2013.01);
(Continued)

(58) Field of Classification Search
CPC .......... A61B 17/07207; A61B 17/2909; A61B 17/068; H02J 7/00
See application file for complete search history.

(56) References Cited

U.S. PATENT DOCUMENTS 2,073,960 A    3/1937  Crosby
2,140,593 A    12/1938 Pankonin
(Continued)

FOREIGN PATENT DOCUMENTS

EP    0 251 444 A1    1/1988
EP    0 492 283 A1    7/1992
(Continued)

OTHER PUBLICATIONS

Ethicon Endo Surgery, Inc., Contour Curved Cutter Stapler, 2014, 2 pgs.
(Continued)

*Primary Examiner* — Nathaniel C Chukwurah
(74) *Attorney, Agent, or Firm* — John F. Heal

(57) ABSTRACT

A powered handle for a surgical stapler can have a drive system including an electric motor. The powered handle can include a manual articulation mechanism to articulate a jaw assembly coupled to a reload shaft connected to the handle. The manual articulation mechanism can include a ball screw mechanism that translates an articulation member responsive to rotation of an articulation knob. The articulation mechanism includes a release function that allows the jaw assembly to return to a longitudinally centered orientation. The powered handle includes a battery pack serving as a power supply for the drive system. A control system can
(Continued)

control actuation of the motor based on user inputs and operating parameters of the stapler. The powered handle can include a manual return mechanism.

15 Claims, 18 Drawing Sheets

Related U.S. Application Data division of application No. 15/486,008, filed on Apr. 12, 2017, now Pat. No. 10,610,225.

(60) Provisional application No. 62/321,629, filed on Apr. 12, 2016.

(51) Int. Cl.
A61B 17/29 (2006.01)
A61B 17/00 (2006.01)
A61B 90/00 (2016.01)
A61B 90/98 (2016.01)

(52) U.S. Cl.
CPC ..... A61B 90/98 (2016.02); A61B 2017/00017 (2013.01); A61B 2017/0046 (2013.01); A61B 2017/00123 (2013.01); A61B 2017/00398 (2013.01); A61B 2017/00407 (2013.01); A61B 2017/00734 (2013.01); A61B 2017/2912 (2013.01); A61B 2017/2922 (2013.01); A61B 2017/2923 (2013.01); A61B 2017/2927 (2013.01); A61B 2090/0803 (2016.02); A61B 2090/0808 (2016.02); A61B 2090/0814 (2016.02); A61B 2560/02 (2013.01); A61B 2560/04 (2013.01)

(56) References Cited

U.S. PATENT DOCUMENTS

| | | |
|---|---|---|
| 2,351,608 A | 6/1944 | Greenwood |
| 2,487,565 A | 11/1949 | Leber et al. |
| 2,641,154 A | 6/1953 | Heller |
| 3,076,373 A | 2/1963 | Matthews |
| 3,077,812 A | 2/1963 | Dietrich |
| 3,080,564 A | 3/1963 | Strekopitov et al. |
| 3,203,220 A | 8/1965 | Kaepernik |
| 3,252,643 A | 5/1966 | Strekopitov et al. |
| 3,273,562 A | 9/1966 | Brown |
| 3,373,646 A | 3/1968 | Ehlert |
| 3,459,187 A | 8/1969 | Pallotta |
| 3,494,533 A | 2/1970 | Green et al. |
| 3,662,939 A | 5/1972 | Bryan |
| 3,675,688 A | 7/1972 | Bryan et al. |
| 3,692,224 A | 9/1972 | Astafiev et al. |
| 4,261,244 A | 4/1981 | Becht et al. |
| 4,281,785 A | 8/1981 | Brooks |
| 4,304,236 A | 12/1981 | Conta et al. |
| 4,312,363 A | 1/1982 | Rothfuss et al. |
| 4,317,451 A | 3/1982 | Cerwin et al. |
| 4,407,286 A | 10/1983 | Noiles et al. |
| 4,434,796 A | 3/1984 | Karapetian et al. |
| 4,442,964 A | 4/1984 | Becht |
| 4,454,875 A | 6/1984 | Pratt et al. |
| 4,522,327 A | 6/1985 | Korthoff et al. |
| 4,527,724 A | 7/1985 | Chow et al. |
| 4,589,582 A | 5/1986 | Bilotti |
| 4,591,085 A | 5/1986 | Di Giovanni |
| 4,606,344 A | 8/1986 | Di Giovanni |
| 4,608,981 A | 9/1986 | Rothfuss et al. |
| 4,610,383 A | 9/1986 | Rothfuss et al. |
| 4,728,020 A | 3/1988 | Green et al. |
| 4,805,823 A | 2/1989 | Rothfuss |
| 4,892,244 A | 1/1990 | Fox et al. |
| 4,923,350 A | 5/1990 | Hinksman et al. |
| 4,941,623 A | 7/1990 | Pruitt |
| 4,955,959 A | 9/1990 | Tompkins et al. |
| 4,978,049 A | 12/1990 | Green |
| 5,031,814 A | 7/1991 | Tompkins et al. |
| 5,065,929 A | 11/1991 | Schulze et al. |
| 5,071,052 A | 12/1991 | Rodak et al. |
| 5,106,008 A | 4/1992 | Tompkins et al. |
| 5,116,349 A | 5/1992 | Aranyi |
| 5,129,570 A | 7/1992 | Schulze et al. |
| 5,201,746 A | 4/1993 | Shichman |
| 5,221,036 A | 6/1993 | Takase |
| 5,236,440 A | 8/1993 | Hlavacek |
| 5,240,163 A | 8/1993 | Stein et al. |
| RE34,519 E | 1/1994 | Fox et al. |
| 5,275,323 A | 1/1994 | Schulze et al. |
| 5,289,963 A | 3/1994 | McGarry et al. |
| D347,474 S | 5/1994 | Olson |
| 5,307,976 A | 5/1994 | Olson et al. |
| 5,308,576 A | 5/1994 | Green et al. |
| 5,326,013 A | 7/1994 | Green et al. |
| 5,350,400 A | 9/1994 | Esposito et al. |
| 5,360,305 A | 11/1994 | Kerrigan |
| 5,364,002 A | 11/1994 | Green et al. |
| 5,366,479 A | 11/1994 | McGarry et al. |
| 5,381,943 A | 1/1995 | Allen et al. |
| 5,389,098 A | 2/1995 | Tsuruta et al. |
| 5,395,034 A | 3/1995 | Allen et al. |
| 5,397,046 A | 3/1995 | Savage et al. |
| 5,413,267 A | 5/1995 | Solyntjes et al. |
| 5,415,334 A | 5/1995 | Williamson, IV et al. |
| 5,415,335 A | 5/1995 | Knodell, Jr. |
| 5,439,155 A | 8/1995 | Viola |
| 5,439,479 A | 8/1995 | Shichman et al. |
| 5,445,304 A | 8/1995 | Plyley et al. |
| 5,447,265 A | 9/1995 | Vidal et al. |
| 5,452,836 A | 9/1995 | Huitema et al. |
| 5,456,401 A | 10/1995 | Green et al. |
| 5,458,279 A | 10/1995 | Plyley |
| 5,462,215 A | 10/1995 | Viola et al. |
| 5,464,144 A | 11/1995 | Guy et al. |
| 5,465,895 A | 11/1995 | Knodel et al. |
| 5,470,006 A | 11/1995 | Rodak |
| 5,470,007 A | 11/1995 | Plyley et al. |
| 5,470,008 A | 11/1995 | Rodak |
| 5,470,009 A | 11/1995 | Rodak |
| 5,472,132 A | 12/1995 | Savage et al. |
| 5,480,089 A | 1/1996 | Blewett |
| 5,485,952 A | 1/1996 | Fontayne |
| 5,487,500 A | 1/1996 | Knodel et al. |
| 5,489,058 A | 2/1996 | Plyley |
| 5,497,933 A | 3/1996 | DeFonzo et al. |
| 5,507,426 A | 4/1996 | Young et al. |
| 5,507,773 A | 4/1996 | Huitema et al. |
| 5,509,596 A | 4/1996 | Green et al. |
| 5,509,920 A | 4/1996 | Phillips et al. |
| 5,529,235 A | 6/1996 | Boiarski et al. |
| 5,547,117 A | 8/1996 | Hamblin et al. |
| 5,553,765 A | 9/1996 | Knodel et al. |
| 5,554,164 A | 9/1996 | Wilson et al. |
| 5,558,266 A | 9/1996 | Green et al. |
| 5,562,241 A | 10/1996 | Knodel et al. |
| 5,562,700 A | 10/1996 | Huitema et al. |
| 5,562,701 A | 10/1996 | Huitema et al. |
| 5,562,702 A | 10/1996 | Huitema et al. |
| 5,564,615 A | 10/1996 | Bishop et al. |
| 5,571,285 A | 11/1996 | Chow et al. |
| 5,579,978 A | 12/1996 | Green et al. |
| 5,580,067 A | 12/1996 | Hamblin et al. |
| 5,584,425 A | 12/1996 | Savage et al. |
| 5,586,711 A | 12/1996 | Plyley et al. |
| 5,588,581 A | 12/1996 | Conlon et al. |
| 5,597,107 A | 1/1997 | Knodel et al. |
| 5,601,224 A | 2/1997 | Bishop et al. |
| 5,605,272 A | 2/1997 | Witt et al. |
| 5,607,095 A | 3/1997 | Smith et al. |
| 5,615,820 A | 4/1997 | Viola |
| 5,626,587 A | 5/1997 | Bishop et al. |
| 5,630,539 A | 5/1997 | Plyley et al. |
| 5,634,584 A | 6/1997 | Okorocha et al. |

(56) References Cited

U.S. PATENT DOCUMENTS

| | | |
|---|---|---|
| 5,636,779 A | 6/1997 | Palmer |
| 5,657,921 A | 8/1997 | Young et al. |
| 5,662,258 A | 9/1997 | Knodel et al. |
| 5,662,662 A | 9/1997 | Bishop et al. |
| 5,662,667 A | 9/1997 | Knodel |
| 5,673,840 A | 10/1997 | Schulze et al. |
| 5,673,841 A | 10/1997 | Schulze et al. |
| 5,673,842 A | 10/1997 | Bittner et al. |
| 5,676,674 A | 10/1997 | Bolanos et al. |
| 5,678,748 A | 10/1997 | Plyley |
| 5,680,982 A | 10/1997 | Schulze et al. |
| 5,680,983 A | 10/1997 | Plyley et al. |
| 5,697,542 A | 12/1997 | Knodel et al. |
| 5,697,543 A | 12/1997 | Burdorff |
| 5,704,534 A | 1/1998 | Huitema et al. |
| 5,704,898 A | 1/1998 | Kokish |
| 5,706,998 A | 1/1998 | Blyley et al. |
| 5,709,334 A | 1/1998 | Sorrentino et al. |
| 5,713,505 A | 2/1998 | Huitema |
| 5,715,988 A | 2/1998 | Palmer |
| 5,718,359 A | 2/1998 | Palmer et al. |
| 5,732,871 A | 3/1998 | Clark et al. |
| 5,735,445 A | 4/1998 | Vidal et al. |
| 5,762,255 A | 6/1998 | Chrisman et al. |
| 5,762,256 A | 6/1998 | Mastri et al. |
| 5,779,130 A | 7/1998 | Alesi et al. |
| 5,782,396 A | 7/1998 | Mastri et al. |
| 5,782,397 A | 7/1998 | Koukline |
| 5,785,232 A | 7/1998 | Vidal et al. |
| 5,794,834 A | 8/1998 | Hamblin et al. |
| 5,797,536 A | 8/1998 | Smith et al. |
| 5,797,537 A | 8/1998 | Oberlin et al. |
| 5,797,538 A | 8/1998 | Heaton et al. |
| 5,810,240 A | 9/1998 | Robertson |
| 5,814,055 A | 9/1998 | Knodel et al. |
| 5,820,009 A | 10/1998 | Melling et al. |
| 5,829,662 A | 11/1998 | Allen et al. |
| 5,860,995 A | 1/1999 | Berkelaar |
| 5,865,361 A | 2/1999 | Milliman et al. |
| 5,878,937 A | 3/1999 | Green et al. |
| 5,878,938 A | 3/1999 | Bittner et al. |
| 5,893,506 A | 4/1999 | Powell |
| 5,894,979 A | 4/1999 | Powell |
| 5,901,895 A | 5/1999 | Heaton et al. |
| 5,918,791 A | 7/1999 | Sorrentino et al. |
| 5,931,847 A | 8/1999 | Bittner et al. |
| 5,954,259 A | 9/1999 | Viola et al. |
| 5,964,394 A | 10/1999 | Robertson |
| D416,089 S | 11/1999 | Barton et al. |
| 5,988,479 A | 11/1999 | Palmer |
| 6,032,849 A | 3/2000 | Mastri et al. |
| 6,053,390 A | 4/2000 | Green et al. |
| 6,079,606 A | 6/2000 | Milliman et al. |
| 6,109,500 A | 8/2000 | Alli et al. |
| 6,131,789 A | 10/2000 | Schulze et al. |
| 6,155,473 A | 12/2000 | Tompkins et al. |
| D441,865 S | 5/2001 | Racenet et al. |
| 6,241,139 B1 | 6/2001 | Milliman et al. |
| 6,250,532 B1 | 6/2001 | Green et al. |
| 6,264,087 B1 | 7/2001 | Whitman |
| 6,270,453 B1 | 8/2001 | Sakai |
| 6,325,810 B1 | 12/2001 | Hamilton et al. |
| 6,330,965 B1 | 12/2001 | Milliman et al. |
| 6,488,196 B1 | 12/2002 | Fenton, Jr. |
| 6,550,757 B2 | 4/2003 | Sesek |
| 6,569,171 B2 | 5/2003 | DeGuillebon et al. |
| 6,595,509 B2 | 7/2003 | Sesek |
| 6,619,529 B2 | 9/2003 | Green et al. |
| 6,644,532 B2 | 11/2003 | Green et al. |
| 6,669,073 B2 | 12/2003 | Milliman et al. |
| 6,716,233 B1 | 4/2004 | Whitman |
| 6,786,382 B1 | 9/2004 | Hoffman |
| 6,817,508 B1 | 11/2004 | Racenet et al. |
| 6,821,282 B2 | 11/2004 | Perry et al. |
| 6,835,199 B2 | 12/2004 | McGuckin, Jr. et al. |
| 6,913,181 B2 | 7/2005 | Mochizuki et al. |
| 6,923,360 B2 | 8/2005 | Sesek et al. |
| 6,953,138 B1 | 10/2005 | Dworak et al. |
| 6,953,139 B2 | 10/2005 | Milliman et al. |
| 6,964,363 B2 | 11/2005 | Wales et al. |
| 6,978,921 B2 | 12/2005 | Shelton, IV et al. |
| 6,986,451 B1 | 1/2006 | Mastri et al. |
| 6,988,649 B2 | 1/2006 | Shelton, IV et al. |
| 7,000,818 B2 | 2/2006 | Shelton, IV et al. |
| 7,044,352 B2 | 5/2006 | Shelton, IV et al. |
| 7,044,353 B2 | 5/2006 | Mastri et al. |
| 7,044,947 B2 | 5/2006 | de la Torre et al. |
| 7,055,730 B2 | 6/2006 | Ehrenfels et al. |
| 7,070,083 B2 | 7/2006 | Jankowski |
| 7,097,089 B2 | 8/2006 | Marczyk |
| 7,097,650 B2 | 8/2006 | Weller et al. |
| 7,108,472 B2 | 9/2006 | Norris et al. |
| 7,128,253 B2 | 10/2006 | Mastri et al. |
| 7,140,527 B2 | 11/2006 | Ehrenfels et al. |
| 7,140,528 B2 | 11/2006 | Shelton, IV |
| 7,143,923 B2 | 12/2006 | Shelton, IV et al. |
| 7,143,924 B2 | 12/2006 | Scirica et al. |
| 7,147,139 B2 | 12/2006 | Schwemberger et al. |
| 7,213,736 B2 | 5/2007 | Wales et al. |
| 7,225,964 B2 | 6/2007 | Mastri et al. |
| 7,237,708 B1 | 7/2007 | Guy et al. |
| 7,258,262 B2 | 8/2007 | Mastri et al. |
| 7,275,674 B2 | 10/2007 | Racenet et al. |
| 7,278,562 B2 | 10/2007 | Mastri et al. |
| 7,290,692 B2 | 11/2007 | Marks |
| 7,293,685 B2 | 11/2007 | Ehrenfels et al. |
| 7,303,107 B2 | 12/2007 | Milliman et al. |
| 7,308,998 B2 | 12/2007 | Mastri et al. |
| 7,328,828 B2 | 2/2008 | Ortiz et al. |
| 7,334,717 B2 | 2/2008 | Rethy et al. |
| 7,380,695 B2 | 6/2008 | Doll et al. |
| 7,380,696 B2 | 6/2008 | Shelton, IV et al. |
| 7,398,908 B2 | 7/2008 | Holsten et al. |
| 7,399,310 B2 | 7/2008 | Edoga et al. |
| 7,401,721 B2 | 7/2008 | Holsten et al. |
| 7,404,508 B2 | 7/2008 | Smith et al. |
| 7,407,075 B2 | 8/2008 | Holsten et al. |
| 7,407,078 B2 | 8/2008 | Shelton, IV et al. |
| 7,416,101 B2 | 8/2008 | Shelton, IV et al. |
| RE40,514 E | 9/2008 | Mastri et al. |
| 7,419,080 B2 | 9/2008 | Smith et al. |
| 7,419,081 B2 | 9/2008 | Ehrenfels et al. |
| 7,422,136 B1 | 9/2008 | Marczyk |
| 7,422,139 B2 | 9/2008 | Shelton, IV et al. |
| 7,431,188 B1 | 10/2008 | Marczyk |
| 7,434,715 B2 | 10/2008 | Shelton, IV et al. |
| 7,434,716 B2 | 10/2008 | Viola |
| 7,455,208 B2 | 11/2008 | Wales et al. |
| 7,455,676 B2 | 11/2008 | Holsten et al. |
| 7,461,767 B2 | 12/2008 | Viola et al. |
| 7,464,846 B2 | 12/2008 | Shelton, IV et al. |
| 7,464,847 B2 | 12/2008 | Viola et al. |
| 7,464,849 B2 | 12/2008 | Shelton, IV et al. |
| 7,467,740 B2 | 12/2008 | Shelton, IV et al. |
| 7,472,814 B2 | 1/2009 | Mastri et al. |
| 7,472,815 B2 | 1/2009 | Shelton, IV et al. |
| 7,472,816 B2 | 1/2009 | Holsten et al. |
| 7,481,348 B2 | 1/2009 | Marczyk |
| 7,481,349 B2 | 1/2009 | Holsten et al. |
| 7,487,899 B2 | 2/2009 | Shelton, IV et al. |
| 7,490,749 B2 | 2/2009 | Schall et al. |
| 7,506,790 B2 | 3/2009 | Shelton, IV |
| 7,506,791 B2 | 3/2009 | Omaits et al. |
| 7,513,408 B2 | 4/2009 | Shelton, IV et al. |
| 7,530,484 B1 | 5/2009 | Durrani |
| 7,543,730 B1 | 6/2009 | Marczyk |
| 7,543,731 B1 | 6/2009 | Green et al. |
| 7,546,940 B2 | 6/2009 | Milliman et al. |
| 7,549,564 B2 | 6/2009 | Boudreaux |
| 7,552,854 B2 | 6/2009 | Wixey et al. |
| 7,556,186 B2 | 7/2009 | Milliman |
| 7,565,993 B2 | 7/2009 | Milliman et al. |
| 7,568,604 B2 | 8/2009 | Ehrenfels et al. |
| 7,588,174 B2 | 9/2009 | Holsten et al. |

(56) References Cited

U.S. PATENT DOCUMENTS

| | | |
|---|---|---|
| 7,588,175 B2 | 9/2009 | Timm et al. |
| 7,588,177 B2 | 9/2009 | Racenet |
| 7,604,151 B2 | 10/2009 | Hess et al. |
| 7,611,038 B2 | 11/2009 | Racenet et al. |
| 7,617,961 B2 | 11/2009 | Viola |
| 7,624,902 B2 | 12/2009 | Marczyk et al. |
| 7,631,793 B2 | 12/2009 | Rethy et al. |
| 7,635,074 B2 | 12/2009 | Olson et al. |
| 7,637,409 B2 | 12/2009 | Marczyk |
| 7,637,410 B2 | 12/2009 | Marczyk |
| 7,641,091 B2 | 1/2010 | Olson et al. |
| 7,641,093 B2 | 1/2010 | Doll et al. |
| 7,641,095 B2 | 1/2010 | Viola |
| 7,644,848 B2 | 1/2010 | Swayze et al. |
| 7,648,055 B2 | 1/2010 | Marczyk |
| 7,651,017 B2 | 1/2010 | Ortiz et al. |
| 7,654,431 B2 | 2/2010 | Hueil et al. |
| 7,658,311 B2 | 2/2010 | Boudreaux |
| 7,665,647 B2 | 2/2010 | Shelton, IV et al. |
| 7,669,746 B2 | 3/2010 | Shelton, IV |
| 7,670,334 B2 | 3/2010 | Hueil et al. |
| 7,673,781 B2 | 3/2010 | Swayze et al. |
| 7,682,367 B2 | 3/2010 | Shah et al. |
| 7,690,547 B2 | 4/2010 | Racenet et al. |
| 7,703,653 B2 | 4/2010 | Shah et al. |
| 7,717,312 B2 | 5/2010 | Beetel |
| 7,721,931 B2 | 5/2010 | Shelton, IV et al. |
| 7,721,933 B2 | 5/2010 | Ehrenfels et al. |
| 7,721,935 B2 | 5/2010 | Racenet et al. |
| 7,721,936 B2 | 5/2010 | Shelton, IV et al. |
| 7,726,538 B2 | 6/2010 | Holsten et al. |
| 7,726,539 B2 | 6/2010 | Holsten et al. |
| 7,731,073 B2 | 6/2010 | Wixey et al. |
| 7,735,703 B2 | 6/2010 | Morgan et al. |
| 7,753,245 B2 | 7/2010 | Boudreaux et al. |
| 7,753,246 B2 | 7/2010 | Scirica |
| 7,757,925 B2 | 7/2010 | Viola et al. |
| 7,766,210 B2 | 8/2010 | Shelton, IV et al. |
| 7,770,774 B2 | 8/2010 | Mastri et al. |
| 7,780,054 B2 | 8/2010 | Wales |
| 7,780,055 B2 | 8/2010 | Scirica et al. |
| 7,784,662 B2 | 8/2010 | Wales et al. |
| 7,784,663 B2 | 8/2010 | Shelton, IV |
| 7,793,812 B2 | 9/2010 | Moore et al. |
| 7,798,386 B2 | 9/2010 | Schall et al. |
| 7,810,693 B2 | 10/2010 | Broehl et al. |
| 7,815,090 B2 | 10/2010 | Marczyk |
| 7,815,091 B2 | 10/2010 | Marczyk |
| 7,819,298 B2 | 10/2010 | Hall et al. |
| 7,819,896 B2 | 10/2010 | Racenet |
| 7,823,760 B2 | 11/2010 | Zemlok et al. |
| 7,828,188 B2 | 11/2010 | Jankowski |
| 7,828,189 B2 | 11/2010 | Holsten et al. |
| 7,837,079 B2 | 11/2010 | Holsten et al. |
| 7,837,081 B2 | 11/2010 | Holsten et al. |
| 7,845,534 B2 | 12/2010 | Viola et al. |
| 7,845,535 B2 | 12/2010 | Scircia |
| 7,845,537 B2 | 12/2010 | Shelton, IV et al. |
| 7,857,184 B2 | 12/2010 | Viola |
| 7,857,185 B2 | 12/2010 | Swayze et al. |
| 7,857,187 B2 | 12/2010 | Milliman |
| 7,861,906 B2 | 1/2011 | Doll et al. |
| 7,866,525 B2 | 1/2011 | Scirica |
| 7,866,527 B2 | 1/2011 | Hall et al. |
| 7,891,534 B2 | 2/2011 | Wenchell et al. |
| 7,905,381 B2 | 3/2011 | Baxter, III et al. |
| 7,909,220 B2 | 3/2011 | Viola |
| 7,909,221 B2 | 3/2011 | Viola et al. |
| 7,913,891 B2 | 3/2011 | Doll et al. |
| 7,914,543 B2 | 3/2011 | Roth et al. |
| 7,918,230 B2 | 4/2011 | Whitman et al. |
| 7,918,376 B1 | 4/2011 | Knodel et al. |
| 7,918,377 B2 | 4/2011 | Measamer et al. |
| 7,922,063 B2 | 4/2011 | Zemlok et al. |
| 7,934,628 B2 | 5/2011 | Wenchell et al. |
| 7,934,629 B2 | 5/2011 | Wixey et al. |
| 7,934,630 B2 | 5/2011 | Shelton, IV et al. |
| 7,942,300 B2 | 5/2011 | Rethy et al. |
| 7,954,685 B2 | 6/2011 | Viola |
| 7,954,686 B2 | 6/2011 | Baxter, III et al. |
| 7,959,050 B2 | 6/2011 | Smith et al. |
| 7,963,433 B2 | 6/2011 | Whitman et al. |
| 7,992,758 B2 | 8/2011 | Whitman et al. |
| 8,002,795 B2 | 8/2011 | Beetel |
| 8,006,887 B2 | 8/2011 | Marczyk |
| 8,007,513 B2 | 8/2011 | Nalagatla et al. |
| 8,008,598 B2 | 8/2011 | Whitman et al. |
| 8,011,550 B2 | 9/2011 | Aranyi et al. |
| 8,011,553 B2 | 9/2011 | Mastri et al. |
| 8,012,170 B2 | 9/2011 | Whitman et al. |
| 8,016,178 B2 | 9/2011 | Olson et al. |
| 8,020,742 B2 | 9/2011 | Marczyk |
| 8,020,743 B2 | 9/2011 | Shelton, IV |
| 8,028,885 B2 | 10/2011 | Smith et al. |
| 8,033,438 B2 | 10/2011 | Scirica |
| 8,033,440 B2 | 10/2011 | Wenchell et al. |
| 8,033,441 B2 | 10/2011 | Marczyk |
| 8,033,442 B2 | 10/2011 | Racenet et al. |
| 8,034,077 B2 | 10/2011 | Smith et al. |
| 8,038,046 B2 | 10/2011 | Smith et al. |
| 8,052,024 B2 | 11/2011 | Viola et al. |
| 8,056,788 B2 | 11/2011 | Mastri et al. |
| 8,056,789 B1 | 11/2011 | White et al. |
| 8,061,576 B2 | 11/2011 | Cappola |
| 8,061,577 B2 | 11/2011 | Racenet et al. |
| 8,070,033 B2 | 12/2011 | Milliman et al. |
| 8,070,034 B1 | 12/2011 | Knodel |
| 8,070,035 B2 | 12/2011 | Holsten et al. |
| 8,070,036 B1 | 12/2011 | Knodel |
| 8,074,861 B2 | 12/2011 | Ehrenfels et al. |
| 8,083,118 B2 | 12/2011 | Milliman et al. |
| 8,087,563 B2 | 1/2012 | Milliman et al. |
| 8,091,753 B2 | 1/2012 | Viola |
| 8,091,754 B2 | 1/2012 | Ehrenfels et al. |
| 8,092,493 B2 | 1/2012 | Marczyk |
| 8,100,309 B2 | 1/2012 | Marczyk |
| 8,113,406 B2 | 2/2012 | Holsten et al. |
| 8,113,407 B2 | 2/2012 | Holsten et al. |
| 8,113,408 B2 | 2/2012 | Wenchell et al. |
| 8,113,410 B2 | 2/2012 | Hall et al. |
| 8,118,207 B2 | 2/2012 | Racenet et al. |
| 8,123,100 B2 | 2/2012 | Holsten et al. |
| 8,127,976 B2 | 3/2012 | Scirica et al. |
| 8,136,712 B2 | 3/2012 | Zingman |
| 8,152,041 B2 | 4/2012 | Kostrzewski |
| 8,157,145 B2 | 4/2012 | Shelton, IV et al. |
| 8,157,150 B2 | 4/2012 | Viola et al. |
| 8,157,152 B2 | 4/2012 | Holsten et al. |
| 8,181,839 B2 | 5/2012 | Beetel |
| 8,186,555 B2 | 5/2012 | Shelton, IV et al. |
| 8,186,556 B2 | 5/2012 | Viola |
| 8,186,560 B2 | 5/2012 | Hess et al. |
| 8,191,752 B2 | 6/2012 | Scirica |
| 8,196,795 B2 | 6/2012 | Moore et al. |
| 8,201,721 B2 | 6/2012 | Zemlok et al. |
| 8,205,619 B2 | 6/2012 | Shah et al. |
| 8,205,780 B2 | 6/2012 | Sorrentino et al. |
| 8,205,781 B2 | 6/2012 | Baxter, III et al. |
| 8,210,411 B2 | 7/2012 | Yates et al. |
| 8,210,416 B2 | 7/2012 | Milliman et al. |
| 8,220,688 B2 | 7/2012 | Laurent et al. |
| 8,225,979 B2 | 7/2012 | Farascioni et al. |
| 8,231,040 B2 | 7/2012 | Zemlok et al. |
| 8,231,041 B2 | 7/2012 | Marczyk et al. |
| 8,235,274 B2 | 8/2012 | Cappola |
| 8,236,010 B2 | 8/2012 | Ortiz et al. |
| 8,240,536 B2 | 8/2012 | Marczyk |
| 8,240,537 B2 | 8/2012 | Marczyk |
| 8,241,322 B2 | 8/2012 | Whitman et al. |
| 8,245,898 B2 | 8/2012 | Smith et al. |
| 8,245,899 B2 | 8/2012 | Swensgard et al. |
| 8,245,900 B2 | 8/2012 | Scirica |
| 8,256,656 B2 | 9/2012 | Milliman et al. |
| 8,272,552 B2 | 9/2012 | Holsten et al. |

(56) References Cited

U.S. PATENT DOCUMENTS

| | | |
|---|---|---|
| 8,272,554 B2 | 9/2012 | Whitman et al. |
| 8,281,972 B2 | 10/2012 | Wixey et al. |
| 8,281,973 B2 | 10/2012 | Wenchell et al. |
| 8,286,846 B2 | 10/2012 | Smith et al. |
| 8,292,146 B2 | 10/2012 | Holsten et al. |
| 8,292,148 B2 | 10/2012 | Viola |
| 8,292,151 B2 | 10/2012 | Viola |
| 8,292,152 B2 | 10/2012 | Milliman et al. |
| 8,292,153 B2 | 10/2012 | Jankowski |
| 8,292,157 B2 | 10/2012 | Smith et al. |
| 8,308,041 B2 | 11/2012 | Kostrzewski |
| 8,308,043 B2 | 11/2012 | Bindra et al. |
| 8,317,070 B2 | 11/2012 | Hueil et al. |
| 8,322,455 B2 | 12/2012 | Shelton, IV et al. |
| 8,336,754 B2 | 12/2012 | Cappola et al. |
| 8,342,377 B2 | 1/2013 | Milliman et al. |
| 8,342,378 B2 | 1/2013 | Marczyk et al. |
| 8,342,379 B2 | 1/2013 | Whitman et al. |
| 8,342,380 B2 | 1/2013 | Viola |
| 8,348,125 B2 | 1/2013 | Viola et al. |
| 8,348,129 B2 | 1/2013 | Bedi et al. |
| 8,348,131 B2 | 1/2013 | Omaits et al. |
| 8,353,440 B2 | 1/2013 | Whitman et al. |
| 8,360,297 B2 | 1/2013 | Shelton, IV et al. |
| 8,360,299 B2 | 1/2013 | Zemlok et al. |
| 8,393,513 B2 | 3/2013 | Jankowski |
| 8,397,972 B2 | 3/2013 | Kostrzewski |
| 8,397,973 B1 | 3/2013 | Hausen |
| 8,403,198 B2 | 3/2013 | Sorrentino et al. |
| 8,413,868 B2 | 4/2013 | Cappola |
| 8,414,577 B2 | 4/2013 | Boudreaux et al. |
| 8,418,906 B2 | 4/2013 | Farascioni et al. |
| 8,418,907 B2 | 4/2013 | Johnson et al. |
| 8,418,908 B1 | 4/2013 | Beardsley |
| 8,419,768 B2 | 4/2013 | Marczyk |
| 8,439,246 B1 | 5/2013 | Knodel |
| 8,444,036 B2 | 5/2013 | Shelton, IV |
| 8,453,907 B2 | 6/2013 | Laurent et al. |
| 8,453,912 B2 | 6/2013 | Mastri et al. |
| 8,453,913 B2 | 6/2013 | Milliman |
| 8,459,520 B2 | 6/2013 | Giordano et al. |
| 8,459,522 B2 | 6/2013 | Marczyk |
| 8,464,922 B2 | 6/2013 | Marczyk |
| 8,469,252 B2 | 6/2013 | Holcomb et al. |
| 8,479,967 B2 | 7/2013 | Marczyk |
| 8,496,152 B2 | 7/2013 | Viola |
| 8,496,155 B2 | 7/2013 | Knodel |
| 8,496,156 B2 | 7/2013 | Sniffin et al. |
| 8,496,683 B2 | 7/2013 | Prommersberger et al. |
| 8,505,799 B2 | 8/2013 | Viola et al. |
| 8,505,801 B2 | 8/2013 | Ehrenfels et al. |
| 8,517,239 B2 | 8/2013 | Scheib et al. |
| 8,517,240 B1 | 8/2013 | Mata et al. |
| 8,523,043 B2 | 9/2013 | Ullrich et al. |
| 8,540,130 B2 | 9/2013 | Moore et al. |
| 8,540,133 B2 | 9/2013 | Bedi et al. |
| 8,540,625 B2 | 9/2013 | Miyoshi |
| 8,544,712 B2 | 10/2013 | Jankowski |
| 8,556,151 B2 | 10/2013 | Viola |
| 8,556,152 B2 | 10/2013 | Marczyk et al. |
| 8,556,153 B1 | 10/2013 | Knodel |
| 8,561,871 B2 | 10/2013 | Rajappa et al. |
| 8,561,874 B2 | 10/2013 | Scirica |
| 8,573,459 B2 | 11/2013 | Smith et al. |
| 8,573,460 B2 | 11/2013 | Cappola |
| 8,573,462 B2 | 11/2013 | Smith et al. |
| 8,573,463 B2 | 11/2013 | Scirica et al. |
| 8,573,464 B2 | 11/2013 | Nalagatla et al. |
| 8,579,176 B2 | 11/2013 | Smith et al. |
| 8,579,177 B2 | 11/2013 | Beetel |
| 8,584,919 B2 | 11/2013 | Hueil et al. |
| 8,584,921 B2 | 11/2013 | Scirica |
| 8,596,513 B2 | 12/2013 | Olson |
| 8,608,043 B2 | 12/2013 | Scirica |
| 8,608,045 B2 | 12/2013 | Smith et al. |
| 8,616,427 B2 | 12/2013 | Viola |
| 8,622,274 B2 | 1/2014 | Yates et al. |
| 8,627,992 B2 | 1/2014 | Edoga et al. |
| 8,627,993 B2 | 1/2014 | Smith et al. |
| 8,627,995 B2 | 1/2014 | Smith et al. |
| 8,631,990 B1 | 1/2014 | Park et al. |
| 8,632,525 B2 | 1/2014 | Kerr et al. |
| 8,632,535 B2 | 1/2014 | Shelton, IV et al. |
| 8,636,189 B1 | 1/2014 | Knodel et al. |
| 8,636,190 B2 | 1/2014 | Zemlok et al. |
| 8,636,192 B2 | 1/2014 | Farascioni et al. |
| 8,636,193 B2 | 1/2014 | Whitman et al. |
| 8,636,762 B2 | 1/2014 | Whitman et al. |
| 8,636,766 B2 | 1/2014 | Milliman et al. |
| 8,657,174 B2 | 2/2014 | Yates et al. |
| 8,657,176 B2 | 2/2014 | Shelton, IV et al. |
| 8,657,178 B2 | 2/2014 | Hueil et al. |
| 8,672,209 B2 | 3/2014 | Crainich |
| 8,672,951 B2 | 3/2014 | Smith et al. |
| 8,685,004 B2 | 4/2014 | Zemlock et al. |
| 8,695,865 B2 | 4/2014 | Smith et al. |
| 8,696,665 B2 | 4/2014 | Hunt et al. |
| 8,708,211 B2 | 4/2014 | Zemlok et al. |
| 8,708,213 B2 | 4/2014 | Shelton, IV et al. |
| 8,740,034 B2 | 6/2014 | Morgan et al. |
| 8,740,035 B2 | 6/2014 | Mastri et al. |
| 8,740,036 B2 | 6/2014 | Williams |
| 8,752,748 B2 | 6/2014 | Whitman et al. |
| 8,763,876 B2 | 7/2014 | Kostrzewski |
| 8,770,458 B2 | 7/2014 | Scirica |
| 8,770,459 B2 | 7/2014 | Racenet et al. |
| 8,789,741 B2 | 7/2014 | Baxter, III et al. |
| 8,800,839 B2 | 8/2014 | Beetel |
| 8,800,840 B2 | 8/2014 | Jankowski |
| 8,800,841 B2 | 8/2014 | Ellerhorst et al. |
| 8,806,973 B2 | 8/2014 | Ross et al. |
| 8,807,414 B2 | 8/2014 | Ross et al. |
| 8,820,603 B2 | 9/2014 | Shelton, IV et al. |
| 8,820,608 B2 | 9/2014 | Miyamoto |
| 8,833,631 B2 | 9/2014 | Munro, III et al. |
| 8,840,003 B2 | 9/2014 | Morgan et al. |
| 8,858,571 B2 | 10/2014 | Shelton, IV et al. |
| 8,875,971 B2 | 11/2014 | Hall et al. |
| 8,875,972 B2 | 11/2014 | Weisenburgh, II et al. |
| 8,887,979 B2 | 11/2014 | Mastri et al. |
| 8,899,462 B2 | 12/2014 | Kostrzewski et al. |
| 8,899,463 B2 | 12/2014 | Schall et al. |
| 8,905,288 B2 | 12/2014 | Wenchell |
| 8,920,435 B2 | 12/2014 | Smith et al. |
| 8,925,783 B2 | 1/2015 | Zemlok et al. |
| 8,931,679 B2 | 1/2015 | Kostrzewski |
| 8,931,683 B2 | 1/2015 | Racenet et al. |
| 8,939,343 B2 | 1/2015 | Milliman et al. |
| 8,967,444 B2 | 3/2015 | Beetel |
| 8,967,446 B2 | 3/2015 | Beardsley et al. |
| 8,967,447 B2 | 3/2015 | Hartoumbekis |
| 8,968,276 B2 | 3/2015 | Zemlok et al. |
| 8,973,803 B2 | 3/2015 | Hall et al. |
| 8,979,827 B2 | 3/2015 | Cappola |
| 9,004,340 B2 | 4/2015 | Scirica |
| 9,010,611 B2 | 4/2015 | Ross et al. |
| 9,016,541 B2 | 4/2015 | Viola et al. |
| 9,016,545 B2 | 4/2015 | Aranyi et al. |
| 9,022,271 B2 | 5/2015 | Scirica |
| 9,023,014 B2 | 5/2015 | Chowaniec et al. |
| 9,027,817 B2 | 5/2015 | Milliman et al. |
| 9,027,818 B2 | 5/2015 | Scirica et al. |
| 9,033,202 B2 | 5/2015 | Scirica |
| 9,038,880 B1 | 5/2015 | Donohoe |
| 9,055,943 B2 | 6/2015 | Zemlok et al. |
| 9,072,515 B2 | 7/2015 | Hall et al. |
| 9,084,601 B2 | 7/2015 | Moore et al. |
| 9,101,358 B2 | 8/2015 | Kerr et al. |
| 9,204,876 B2 | 12/2015 | Cappola et al. |
| 9,237,890 B2 | 1/2016 | Kostrzewski |
| 9,265,585 B2 | 2/2016 | Wingardner et al. |
| 9,282,966 B2 | 3/2016 | Shelton, IV et al. |
| 9,386,984 B2 | 7/2016 | Aronhalt et al. |
| 9,402,629 B2 | 8/2016 | Ehrenfels et al. |

(56) References Cited

U.S. PATENT DOCUMENTS

| | | |
|---|---|---|
| 9,510,830 B2 | 12/2016 | Shelton, IV et al. |
| 9,532,782 B2 | 1/2017 | Kostrzewski |
| 9,662,108 B2 | 5/2017 | Williams |
| 9,737,302 B2 | 8/2017 | Shelton, IV et al. |
| 9,737,303 B2 | 8/2017 | Shelton, IV et al. |
| 9,797,486 B2 | 10/2017 | Zergiebel et al. |
| 2002/0025243 A1 | 2/2002 | Heck |
| 2002/0029044 A1 | 3/2002 | Monassevitch et al. |
| 2002/0062136 A1 | 5/2002 | Hillstead |
| 2002/0120279 A1 | 8/2002 | Deguillebon et al. |
| 2003/0130677 A1 | 7/2003 | Whitman et al. |
| 2004/0006372 A1 | 1/2004 | Racenet et al. |
| 2004/0138705 A1 | 7/2004 | Heino et al. |
| 2005/0234478 A1 | 10/2005 | Wixey |
| 2006/0097026 A1 | 5/2006 | Shelton, IV |
| 2006/0100644 A1 | 5/2006 | Viola |
| 2006/0180634 A1 | 8/2006 | Shelton, IV et al. |
| 2006/0235442 A1 | 10/2006 | Huitema |
| 2006/0289602 A1 | 12/2006 | Wales et al. |
| 2007/0034664 A1 | 2/2007 | Jiang |
| 2007/0039997 A1 | 2/2007 | Mather et al. |
| 2007/0057014 A1 | 3/2007 | Whitman et al. |
| 2007/0068990 A1 | 3/2007 | Shelton, IV et al. |
| 2007/0084897 A1 | 4/2007 | Shelton, IV et al. |
| 2007/0102472 A1 | 5/2007 | Shelton, IV |
| 2007/0119901 A1 | 5/2007 | Ehrenfels et al. |
| 2007/0131732 A1 | 6/2007 | Holsten et al. |
| 2007/0175950 A1 | 8/2007 | Shelton, IV et al. |
| 2007/0175951 A1 | 8/2007 | Shelton, IV et al. |
| 2008/0029574 A1 | 2/2008 | Shelton et al. |
| 2008/0029575 A1 | 2/2008 | Shelton et al. |
| 2008/0041918 A1 | 2/2008 | Holsten et al. |
| 2008/0078807 A1 | 4/2008 | Hess et al. |
| 2008/0083807 A1 | 4/2008 | Beardsley et al. |
| 2008/0169333 A1 | 7/2008 | Shelton et al. |
| 2008/0179375 A1 | 7/2008 | Scirica |
| 2008/0255607 A1 | 10/2008 | Zemlok |
| 2009/0001129 A1 | 1/2009 | Marczyk |
| 2009/0001130 A1 | 1/2009 | Hess et al. |
| 2009/0026245 A1 | 1/2009 | Holsten et al. |
| 2009/0048589 A1 | 2/2009 | Takashino et al. |
| 2009/0057369 A1 | 3/2009 | Smith et al. |
| 2009/0090763 A1 | 4/2009 | Zemlok et al. |
| 2009/0198272 A1 | 8/2009 | Kerver et al. |
| 2009/0206131 A1 | 8/2009 | Weisenburgh, II et al. |
| 2009/0206133 A1 | 8/2009 | Morgan et al. |
| 2009/0206137 A1 | 8/2009 | Hall et al. |
| 2009/0277948 A1 | 11/2009 | Beardsley et al. |
| 2009/0277949 A1 | 11/2009 | Viola et al. |
| 2010/0069942 A1 | 3/2010 | Shelton, IV |
| 2010/0072258 A1 | 3/2010 | Farascioni et al. |
| 2010/0089970 A1 | 4/2010 | Smith et al. |
| 2010/0193566 A1 | 8/2010 | Scheib et al. |
| 2010/0230465 A1 | 9/2010 | Smith et al. |
| 2010/0331820 A1 | 12/2010 | Prisco et al. |
| 2011/0036892 A1 | 2/2011 | Marczyk et al. |
| 2011/0042440 A1 | 2/2011 | Holsten et al. |
| 2011/0087276 A1 | 4/2011 | Bedi et al. |
| 2011/0108601 A1 | 5/2011 | Clark et al. |
| 2011/0108603 A1 | 5/2011 | Racenet et al. |
| 2011/0121049 A1 | 5/2011 | Malinouskas et al. |
| 2011/0125138 A1 | 5/2011 | Malinouskas et al. |
| 2011/0127185 A1 | 6/2011 | Ward |
| 2011/0139852 A1 | 6/2011 | Zingman |
| 2011/0147433 A1 | 6/2011 | Shelton, IV et al. |
| 2011/0155787 A1 | 6/2011 | Baxter, III et al. |
| 2011/0290853 A1 | 12/2011 | Shelton, IV et al. |
| 2012/0061446 A1 | 3/2012 | Knodel et al. |
| 2012/0074198 A1 | 3/2012 | Huitema et al. |
| 2012/0074200 A1 | 3/2012 | Schmid et al. |
| 2012/0078243 A1 | 3/2012 | Worrell et al. |
| 2012/0080482 A1 | 4/2012 | Schall et al. |
| 2012/0080498 A1 | 4/2012 | Shelton, IV et al. |
| 2012/0091182 A1 | 4/2012 | Marczyk |
| 2012/0168487 A1 | 7/2012 | Holsten et al. |
| 2012/0193396 A1 | 8/2012 | Zemlok et al. |
| 2012/0211542 A1 | 8/2012 | Racenet |
| 2012/0286022 A1 | 11/2012 | Olson et al. |
| 2012/0318844 A1 | 12/2012 | Shelton, IV et al. |
| 2012/0325893 A1 | 12/2012 | Pastorelli et al. |
| 2013/0001270 A1 | 1/2013 | Kostrzewski |
| 2013/0015229 A1 | 1/2013 | Viola |
| 2013/0015230 A1 | 1/2013 | Wixey et al. |
| 2013/0015232 A1 | 1/2013 | Smith et al. |
| 2013/0015233 A1 | 1/2013 | Viola |
| 2013/0020375 A1 | 1/2013 | Shelton, IV et al. |
| 2013/0037595 A1 | 2/2013 | Gupta et al. |
| 2013/0048697 A1 | 2/2013 | Shelton, IV et al. |
| 2013/0056521 A1 | 3/2013 | Swensgard |
| 2013/0079814 A1 | 3/2013 | Hess et al. |
| 2013/0087603 A1 | 4/2013 | Viola |
| 2013/0092717 A1 | 4/2013 | Marczyk et al. |
| 2013/0098964 A1 | 4/2013 | Smith et al. |
| 2013/0098965 A1 | 4/2013 | Kostrzewski et al. |
| 2013/0098969 A1 | 4/2013 | Scirica et al. |
| 2013/0105545 A1 | 5/2013 | Burbank |
| 2013/0105547 A1 | 5/2013 | Beardsley |
| 2013/0105548 A1 | 5/2013 | Hodgkinson et al. |
| 2013/0105549 A1 | 5/2013 | Holsten et al. |
| 2013/0112730 A1 | 5/2013 | Whitman et al. |
| 2013/0112731 A1 | 5/2013 | Hodgkinson |
| 2013/0126583 A1 | 5/2013 | Hueil et al. |
| 2013/0126586 A1 | 5/2013 | Zhang et al. |
| 2013/0146640 A1 | 6/2013 | Jankowski |
| 2013/0172928 A1 | 7/2013 | Kostrzewski |
| 2013/0172929 A1 | 7/2013 | Hess et al. |
| 2013/0175317 A1 | 7/2013 | Yates et al. |
| 2013/0175322 A1 | 7/2013 | Yates et al. |
| 2013/0184718 A1 | 7/2013 | Smith et al. |
| 2013/0186931 A1 | 7/2013 | Beardsley |
| 2013/0186932 A1 | 7/2013 | Shelton, IV et al. |
| 2013/0186933 A1 | 7/2013 | Shelton, IV et al. |
| 2013/0193188 A1 | 8/2013 | Shelton, IV et al. |
| 2013/0200132 A1 | 8/2013 | Moore et al. |
| 2013/0206816 A1 | 8/2013 | Penna |
| 2013/0214025 A1 | 8/2013 | Zemlok et al. |
| 2013/0221065 A1 | 8/2013 | Aronhalt et al. |
| 2013/0240604 A1 | 9/2013 | Knodel |
| 2013/0248582 A1 | 9/2013 | Scirica |
| 2013/0256370 A1 | 10/2013 | Smith et al. |
| 2013/0256371 A1 | 10/2013 | Shelton, IV |
| 2013/0270321 A1 | 10/2013 | Marczyk |
| 2013/0270323 A1 | 10/2013 | Marczyk |
| 2013/0284789 A1 | 10/2013 | Smith et al. |
| 2013/0284791 A1 | 10/2013 | Olson et al. |
| 2013/0299552 A1 | 11/2013 | Viola |
| 2013/0306702 A1 | 11/2013 | Viola et al. |
| 2013/0306703 A1 | 11/2013 | Ehrenfels et al. |
| 2013/0306706 A1 | 11/2013 | Knodel |
| 2013/0313303 A1 | 11/2013 | Shelton, IV et al. |
| 2013/0327809 A1 | 12/2013 | Shelton, IV et al. |
| 2013/0327810 A1 | 12/2013 | Swayze et al. |
| 2013/0334278 A1 | 12/2013 | Kerr et al. |
| 2013/0334280 A1 | 12/2013 | Krehel et al. |
| 2013/0334281 A1 | 12/2013 | Williams |
| 2013/0334283 A1 | 12/2013 | Swayze et al. |
| 2013/0334284 A1 | 12/2013 | Swayze et al. |
| 2013/0334285 A1 | 12/2013 | Swayze et al. |
| 2013/0334286 A1 | 12/2013 | Swayze et al. |
| 2013/0334287 A1 | 12/2013 | Shelton, IV |
| 2013/0334288 A1 | 12/2013 | Shelton, IV |
| 2014/0014704 A1 | 1/2014 | Onukuri et al. |
| 2014/0014707 A1 | 1/2014 | Onukuri et al. |
| 2014/0021239 A1 | 1/2014 | Kostrzewski |
| 2014/0025046 A1 | 1/2014 | Williams et al. |
| 2014/0027491 A1 | 1/2014 | Beardsley et al. |
| 2014/0027493 A1 | 1/2014 | Jankowski |
| 2014/0042204 A1 | 2/2014 | Beetel |
| 2014/0103092 A1 | 4/2014 | Kostrzewski et al. |
| 2014/0103093 A1 | 4/2014 | Koch, Jr. et al. |
| 2014/0107640 A1 | 4/2014 | Yates et al. |
| 2014/0110453 A1 | 4/2014 | Wingardner et al. |
| 2014/0131416 A1 | 5/2014 | Whitman et al. |
| 2014/0135832 A1 | 5/2014 | Park et al. |

(56) References Cited

U.S. PATENT DOCUMENTS

| | | |
|---|---|---|
| 2014/0151433 A1 | 6/2014 | Shelton, IV et al. |
| 2014/0151434 A1 | 6/2014 | Shelton, IV et al. |
| 2014/0158746 A1 | 6/2014 | Mastri et al. |
| 2014/0166727 A1 | 6/2014 | Swayze et al. |
| 2014/0175146 A1 | 6/2014 | Knodel |
| 2014/0175149 A1 | 6/2014 | Smith et al. |
| 2014/0203063 A1 | 7/2014 | Hessler et al. |
| 2014/0205637 A1 | 7/2014 | Widenhouse et al. |
| 2014/0224856 A1 | 8/2014 | Smith et al. |
| 2014/0236173 A1 | 8/2014 | Scirica et al. |
| 2014/0236184 A1 | 8/2014 | Leimbach |
| 2014/0239038 A1 | 8/2014 | Leimbach et al. |
| 2014/0239041 A1 | 8/2014 | Zerkle et al. |
| 2014/0239044 A1 | 8/2014 | Hoffman |
| 2014/0246474 A1 | 9/2014 | Hall et al. |
| 2014/0246475 A1 | 9/2014 | Hall et al. |
| 2014/0246478 A1 | 9/2014 | Baber et al. |
| 2014/0246479 A1 | 9/2014 | Baber et al. |
| 2014/0260746 A1 | 9/2014 | Sakaguchi et al. |
| 2014/0263537 A1 | 9/2014 | Leimbach et al. |
| 2014/0263539 A1 | 9/2014 | Leimbach et al. |
| 2014/0263541 A1 | 9/2014 | Leimbach et al. |
| 2014/0263542 A1 | 9/2014 | Leimbach et al. |
| 2014/0263543 A1 | 9/2014 | Leimbach et al. |
| 2014/0263545 A1 | 9/2014 | Williams et al. |
| 2014/0263546 A1 | 9/2014 | Aranyi |
| 2014/0263550 A1 | 9/2014 | Aranyi et al. |
| 2014/0263553 A1* | 9/2014 | Leimbach ............ A61B 17/072 227/176.1 |
| 2014/0263554 A1 | 9/2014 | Leimbach et al. |
| 2014/0263555 A1 | 9/2014 | Hufnagel et al. |
| 2014/0263559 A1 | 9/2014 | Williams et al. |
| 2014/0263562 A1* | 9/2014 | Patel ................ A61B 17/07207 227/176.1 |
| 2014/0263564 A1 | 9/2014 | Leimbach et al. |
| 2014/0263565 A1 | 9/2014 | Lytle, IV et al. |
| 2014/0263566 A1 | 9/2014 | Williams et al. |
| 2014/0263567 A1 | 9/2014 | Williams et al. |
| 2014/0263568 A1 | 9/2014 | Williams et al. |
| 2014/0263569 A1 | 9/2014 | Williams et al. |
| 2014/0263570 A1 | 9/2014 | Hopkins et al. |
| 2014/0263571 A1 | 9/2014 | Morgan et al. |
| 2014/0263572 A1 | 9/2014 | Shelton, IV et al. |
| 2014/0284372 A1 | 9/2014 | Kostrzewski |
| 2014/0291378 A1 | 10/2014 | Shelton, IV et al. |
| 2014/0299649 A1 | 10/2014 | Shelton, IV et al. |
| 2014/0305986 A1 | 10/2014 | Hall et al. |
| 2014/0305988 A1 | 10/2014 | Boudreaux et al. |
| 2014/0305992 A1 | 10/2014 | Kimsey et al. |
| 2014/0305994 A1 | 10/2014 | Parihar et al. |
| 2014/0353359 A1 | 12/2014 | Hall et al. |
| 2015/0008248 A1 | 1/2015 | Giordano et al. |
| 2015/0034697 A1 | 2/2015 | Mastri et al. |
| 2015/0041518 A1 | 2/2015 | Shelton, IV et al. |
| 2015/0053738 A1 | 2/2015 | Morgan et al. |
| 2015/0053740 A1 | 2/2015 | Shelton, IV |
| 2015/0053741 A1 | 2/2015 | Shelton, IV et al. |
| 2015/0053742 A1 | 2/2015 | Shelton, IV et al. |
| 2015/0053743 A1 | 2/2015 | Yates et al. |
| 2015/0053744 A1 | 2/2015 | Swayze et al. |
| 2015/0053745 A1 | 2/2015 | Yates et al. |
| 2015/0053746 A1 | 2/2015 | Shelton, IV et al. |
| 2015/0053748 A1 | 2/2015 | Yates et al. |
| 2015/0053749 A1 | 2/2015 | Shelton, IV et al. |
| 2015/0054753 A1 | 2/2015 | Morgan et al. |
| 2015/0060516 A1 | 3/2015 | Collings et al. |
| 2015/0060517 A1 | 3/2015 | Williams |
| 2015/0060521 A1 | 3/2015 | Weisenburgh, II et al. |
| 2015/0076205 A1 | 3/2015 | Zergiebel |
| 2015/0076206 A1 | 3/2015 | Sapre |
| 2015/0076209 A1 | 3/2015 | Shelton, IV et al. |
| 2015/0076210 A1 | 3/2015 | Shelton, IV et al. |
| 2015/0076212 A1 | 3/2015 | Shelton, IV |
| 2015/0083781 A1 | 3/2015 | Giordano et al. |
| 2015/0083783 A1 | 3/2015 | Shelton, IV et al. |
| 2015/0090760 A1 | 4/2015 | Giordano et al. |
| 2015/0090761 A1 | 4/2015 | Giordano et al. |
| 2015/0090762 A1 | 4/2015 | Giordano et al. |
| 2015/0090764 A1 | 4/2015 | Zemlok et al. |
| 2015/0108201 A1 | 4/2015 | Williams |
| 2015/0122872 A1 | 5/2015 | Olson et al. |
| 2015/0127046 A1 | 5/2015 | Peterson |
| 2015/0129631 A1 | 5/2015 | Beetel |
| 2015/0129634 A1 | 5/2015 | Shelton, IV et al. |
| 2015/0133995 A1 | 5/2015 | Shelton, IV et al. |
| 2015/0133996 A1 | 5/2015 | Shelton, IV et al. |
| 2015/0134076 A1 | 5/2015 | Shelton, IV et al. |
| 2015/0144678 A1 | 5/2015 | Hall et al. |
| 2015/0201935 A1 | 7/2015 | Weisenburgh, II et al. |
| 2015/0208902 A1 | 7/2015 | Okamoto |
| 2015/0245834 A1 | 9/2015 | Scirica et al. |
| 2015/0272576 A1 | 10/2015 | Cappola |
| 2015/0289873 A1 | 10/2015 | Shelton, IV et al. |
| 2015/0297221 A1 | 10/2015 | Kerr et al. |
| 2015/0297233 A1 | 10/2015 | Huitema et al. |
| 2016/0000439 A1 | 1/2016 | Weisenburgh, II et al. |
| 2016/0000440 A1 | 1/2016 | Weisenburgh, II et al. |
| 2016/0058447 A1 | 3/2016 | Posada et al. |
| 2016/0183948 A1 | 6/2016 | Shelton, IV et al. |
| 2016/0338702 A1 | 11/2016 | Ehrenfels et al. |
| 2016/0374672 A1 | 12/2016 | Bear et al. |
| 2016/0374675 A1 | 12/2016 | Shelton, IV et al. |
| 2017/0007241 A1 | 1/2017 | Shelton, IV et al. |
| 2017/0007242 A1 | 1/2017 | Shelton, IV et al. |
| 2017/0007243 A1 | 1/2017 | Shelton, IV et al. |
| 2017/0007249 A1 | 1/2017 | Shelton, IV et al. |
| 2017/0231633 A1 | 8/2017 | Marczyk et al. |
| 2017/0245856 A1 | 8/2017 | Baxter, III et al. |
| 2017/0245858 A1 | 8/2017 | Williams |
| 2017/0281161 A1 | 10/2017 | Shelton, IV et al. |
| 2017/0281165 A1 | 10/2017 | Harris et al. |
| 2017/0281168 A1 | 10/2017 | Shelton, IV et al. |
| 2017/0290583 A1 | 10/2017 | Reed et al. |
| 2017/0290584 A1 | 10/2017 | Jasemian et al. |

FOREIGN PATENT DOCUMENTS

| | | |
|---|---|---|
| EP | 0 514 139 A2 | 11/1992 |
| EP | 0 536 903 A2 | 4/1993 |
| EP | 0 596 543 A1 | 5/1994 |
| EP | 1 523 944 A1 | 4/2005 |
| EP | 1 759 812 A1 | 3/2007 |
| EP | 1 915 953 A1 | 4/2008 |
| EP | 1 479 348 B1 | 7/2008 |
| EP | 2 005 902 A2 | 12/2008 |
| EP | 2 090 241 A1 | 8/2009 |
| EP | 2 263 568 A2 | 12/2010 |
| EP | 2 361 562 A1 | 8/2011 |
| EP | 2 462 875 A2 | 6/2012 |
| EP | 2 486 859 A2 | 8/2012 |
| EP | 2 764 833 A2 | 8/2014 |
| EP | 2 772 192 A1 | 9/2014 |
| EP | 2 777 530 A1 | 9/2014 |
| EP | 2 923 661 A2 | 3/2015 |
| EP | 2 891 462 A1 | 7/2015 |
| EP | 2 926 742 A1 | 10/2015 |
| EP | 2 942 020 A2 | 11/2015 |
| EP | 3 135 225 A2 | 3/2017 |
| EP | 3 238 639 A2 | 3/2017 |
| EP | 3 338 653 A1 | 6/2018 |
| EP | 3 338 698 A1 | 6/2018 |
| EP | 3 338 702 A1 | 6/2018 |
| JP | 2001-087272 A | 4/2001 |
| RU | 2063710 | 7/1996 |
| WO | WO 83/02247 A1 | 7/1983 |
| WO | WO 94/24947 A1 | 11/1994 |
| WO | WO 02/30296 A2 | 4/2002 |
| WO | WO 02/096327 A2 | 12/2002 |
| WO | WO 2003/094747 A1 | 11/2003 |
| WO | WO 2004/032762 A1 | 4/2004 |
| WO | WO 2012/052729 A1 | 4/2012 |
| WO | WO 2014/139440 A1 | 9/2014 |

(56) References Cited

FOREIGN PATENT DOCUMENTS

OTHER PUBLICATIONS

Justright Surgical, JustRight Surgery, Dec. 31, 2014, 2 pgs.
European Patent Office, The International Search Report and the Written Opinion of the International Searching Authority for International Application No. PCT/US2014/028811, entitled "Surgical Stapler Having Actuation Mechanism with Rotatable Shaft," dated Aug. 5, 2014, 14 pgs.
The International Bureau of WIPO, International Preliminary Report on Patentability, for International Application No. PCT/US2014/028811, entitled "Surgical Stapler Having Actuation Mechanism with Rotatable Shaft," dated Sep. 15, 2015, 11 pgs.
European Patent Office, European Search Report for European Application No. EP 14764812.5, entitled "Surgical Stapler Having Actuation Mechanism with Rotatable Shaft," dated Apr. 6, 2017, 6 pgs.
International Searching Authority/ EPO, Invitation to Pay Additional Fees and Communication Relating to the Results of the Partial International Search for PCT/US2017/027269, entitled "Reload Shaft Assembly for Surgical Stapler," dated Jun. 28, 2017, 15 pgs.
International Searching Authority/ EPO, Invitation to Pay Additional Fees and Communication Relating to the Results of the Partial International Search for PCT/US2017/027213, entitled "Surgical Stapler Having a Powered Handle," dated Jul. 5, 2017, 11 pgs.
International Searching Authority/ EPO, Invitation to Pay Additional Fees and Communication Relating to the Results of the Partial International Search for PCT/US2017/027142, entitled "Surgical Stapler Having Articulation Mechanism," dated Jul. 10, 2017, 15 pgs.
European Patent Office, The International Search Report and the Written Opinion of the International Searching Authority for International Application No. PCT/US2017/027269, entitled "Reload Shaft Assembly for Surgical Stapler," dated Sep. 12, 2017, 22 pgs.
European Patent Office, The International Search Report and the Written Opinion of the International Searching Authority for International Application No. PCT/US2017/027213, entitled "Surgical Stapler Having a Powered Handle," dated Sep. 13, 2017, 17 pgs.
European Patent Office, The International Search Report and the Written Opinion of the International Searching Authority for International Application No. PCT/US2017/027142, entitled "Surgical Stapler Having Articulation Mechanism," dated Sep. 14, 2017, 21 pgs.
European Patent Office, The International Search Report and Written Opinion of the International Searching Authority for International Application No. PCT/US2016/045993 titled "Surgical Stapler Having Locking Articulation Joint", dated Jan. 24, 2017, 20 pgs.
The International Bureau of WIPO, International Preliminary Report on Patentability, for International Application No. PCT/US2016/045993, entitled "Surgical Stapler Having Locking Articulation Joint," dated Feb. 15, 2018, 13 pgs.
European Patent Office, European Search Report for European Application No. 07784007.2, entitled "Surgical Stapler," dated Jun. 15, 2012, 6 pgs.
International Searching Authority, U.S., The International Search Report and the Written Opinion of the International Searching authority for international application PCT/US2014/027768, titled "Surgical Stapler with Expandable Jaw", dated Jul. 25, 2014, 17 pgs.
European Patent Office, International Search Report and Written Opinion for International Application No. PCT/US2014/028211, entitled "Surgical Stapler with Partial Pockets," dated Sep. 8, 2014, 17 pgs.
International Searching Authority, U.S., The International Search Report and the Written Opinion of the International Searching authority for international application PCT/US2015/0035379, titled "Surgical Stapler with Circumferential Firing", dated Sep. 15, 2015, 22 pgs.
The International Bureau of WIPO, International Preliminary Report on Patentability, for International Application No. PCT/US2014/027768, entitled "Surgical Stapler with Expandable Jaw," dated Sep. 24, 2015, 9 pgs.
The International Bureau of WIPO, International Preliminary Report on Patentability for International Application No. PCT/US2015/035379, entitled "Surgical Stapler with Circumferential Firing," dated Dec. 22, 2016, 14 pgs.
European Patent Office, International Search Report and Written Opinion for International Application No. PCT/US2015/050103 titled "Surgical Stapler with Self-Adjusting Staple Height" dated Feb. 17, 2016, 18 pgs.
The International Bureau of WIPO, International Preliminary Report on Patentability for International Application No. PCT/US2015/050103, titled "Surgical Stapler With Self-Adjusting Staple Height," dated Mar. 30, 2017, 12 pgs.
European Patent Office, Partial European Search Report for European Application No. EP 14762896.0, entitled "Surgical Stapler with Expandable Jaw," dated Apr. 10, 2017, 6 pgs.
European Patent Office, Extended European Search Report for European Application No. EP 18186558.5, entitled "Surgical Stapler with Partial Pockets," dated Oct. 10, 2018, 9 pgs.
The International Bureau of WIPO, International Preliminary Report on Patentability, for International Application No. PCT/US2017/027142, entitled "Surgical Stapler Having Articulation Mechanism," dated Oct. 25, 2018, 12 pgs.
The International Bureau of WIPO, International Preliminary Report on Patentability, for International Application No. PCT/US2017/027213, entitled "Surgical Stapler Having Powered Handle," dated Oct. 25, 2018, 9 pgs.
The International Bureau of WIPO, International Preliminary Report on Patentability, for International Application No. PCT/US2017/027269, entitled "Reload Shaft Assembly for Surgical Stapler," dated Oct. 25, 2018, 12 pgs.
European Patent Office, Extended European Search Report for European Application No. EP 18189960.0, entitled "Surgical Stapler with Expandable Jaw," dated Dec. 13, 2018, 6 pgs.
International Searching Authority/ EPO, Invitation to Pay Additional Fees and Communication Relating to the Results of the Partial International Search for PCT/US2019/019867, entitled "Surgical Stapler Having a Powered Handle," dated May 24, 2019, 19 pgs.
European Patent Office, The International Search Report and the Written Opinion of the International Searching Authority for International Application No. PCT/US2019/019867, entitled "Surgical Stapler Having a Powered Handle," dated Jul. 19, 2019, 24 pgs.
European Patent Office, Extended European Search Report for European Application No. EP 19150575.9, entitled "Surgical Stapler Having Actuation Mechanism with Rotatable Shaft," dated Aug. 21, 2019, 5 pgs.
European Patent Office, Extended European Search Report for European Application No. EP 19180055.6, entitled "Surgical Stapler with Circumferential Firing," dated Sep. 20, 2019, 8 pgs.
European Patent Office, The International Search Report and the Written Opinion of the International Searching Authority for International Application No. PCT/US2020/019938, entitled "Surgical Stapling Instrument Having a Two-Position Mechanism," dated Jun. 18, 2020, 16 pgs.
European Patent Office, Extended European Search Report for European Application No. EP 20157713.7, entitled "Surgical Stapler with Expandable Jaw," dated May 11, 2020, 6 pgs.
International Searching Authority/ EPO, Invitation to Pay Additional Fees for PCTUS2020/025496, entitled "Reload Cover for Surgical Stapling System," dated Jun. 18, 2019, 15 pgs.
European Patent Office, Extended European Search Report for European Application No. EP 20161294.2, entitled "Surgical Stapler with Self-Adjusting Staple Height," dated Jun. 22, 2020, 6 pgs.
European Patent Office, Extended European Search Report for European Application No. EP 20197859.0, entitled "Surgical Stapler with Circumferential Firing," dated Jan. 28, 2021, 13 pgs.
European Patent Office, The International Search Report and the Written Opinion of the International Searching Authority for International Application No. PCT/US2020/025496, entitled "Reload Cover for Surgical Stapling System," dated Aug. 13, 2020, 20 pgs.

(56) References Cited

OTHER PUBLICATIONS

The International Bureau of WIPO, International Preliminary Report on Patentability, for International Application No. PCT/US2019/019867, entitled "Surgical Stapler Having a Powered Handle," dated Sep. 3, 2020, 16 pgs.

\* cited by examiner

SURGICAL STAPLER HAVING A POWERED HANDLE

CROSS REFERENCE TO RELATED APPLICATIONS

This application is a continuation of U.S. patent application Ser. No. 16/821,830, entitled "SURGICAL STAPLER HAVING A POWERED HANDLE," filed Mar. 17, 2020 which issued as U.S. Pat. No. 11,272,934, and which is a division of U.S. patent application Ser. No. 15/486,008, entitled "SURGICAL STAPLER HAVING A POWERED HANDLE," filed Apr. 12, 2017 which issued as U.S. Pat. No. 10,610,225, and which claims the benefit of U.S. Provisional Patent Application Ser. No. 62/321,629, entitled "SURGICAL STAPLER HAVING A POWERED HANDLE," filed Apr. 12, 2016. The above-referenced applications are incorporated by reference herein in their entireties.

BACKGROUND OF THE INVENTION

Field of the Invention

The present application relates generally to surgical occlusion instruments and, more particularly, to powered surgical staplers.

Description of the Related Art

Surgical staplers are used to approximate or clamp tissue and to staple the clamped tissue together. As such, surgical staplers have mechanisms to ensure that tissue is properly positioned and captured and to drive staples through the tissue. As a result, this has produced, for example, multiple triggers and handles in conjunction with complex mechanisms to provide proper stapling of the clamped tissue. With these complex mechanisms, surgical staplers can have increased manufacturing burdens, as well as potential sources for device failure and confusion for the user. Thus, reliable stapling of clamped tissue without complex mechanisms is desired.

SUMMARY OF THE INVENTION

In certain embodiments, a powered handle for a surgical stapling system is provided herein. The powered handle can comprise a drive system powered by a power supply to selectively actuate an actuation adapter. The powered handle can comprise a manual articulation mechanism to selectively actuate an articulation adapter. The powered handle can further comprise a coupler having a bayonet coupling to simultaneously couple the articulation adapter and the actuation adapter to an articulation member and a drive member in a reload shaft.

In certain embodiments, the powered handle of the surgical stapling system comprises a control system to actuate the drive system responsive to user input from a movable trigger and a fire/return button on the powered handle. The control system can further vary an actuation profile of the drive system responsive to various operating parameters including the drive system operating torque, a longitudinal position of the actuation adapter, and identification of a jaw assembly length or configuration.

In certain embodiments, the powered handle of the surgical stapling system comprises a manual articulation system including a ball screw mechanism. The ball screw mechanism can allow continuous articulation of a jaw assembly of the stapling system within a predetermined articulation range. The ball screw mechanism can be biased to a longitudinally centered position and be rapidly centered through the use of a release mechanism.

In certain embodiments, a handle assembly for a surgical stapler is provided. The handle assembly comprises a handle body, an electric motor, an actuation shaft and a mechanical return mechanism. The handle body comprises a stationary handle and a trigger pivotably coupled to the handle body. The electric motor is disposed within the handle body. The actuation shaft is slidable within the handle body along a longitudinal axis and rotatable within the handle body about the longitudinal axis. The actuation shaft comprises a rack formed thereon. The actuation shaft is rotatable from a first position wherein the rack is operationally engaged with the electric motor to longitudinally slide the actuation shaft to a second position wherein the rack is disengaged from the electric motor and engaged with the manual return mechanism.

In certain embodiments, a handle assembly for a surgical stapler is provided. The handle assembly comprises a handle body, an electric motor, an actuation shaft, a motor gear, an auxiliary gear, a crown gear, a potentiometer, and a control system. The handle body comprising a stationary handle and a trigger pivotably coupled to the handle body. The electric motor is disposed within the handle body. The motor comprises an output shaft. The actuation shaft is slidable within the handle body along a longitudinal axis. The motor gear is coupled to the output shaft of the motor. The auxiliary gear is in driven engagement with the motor gear. The auxiliary gear is operatively engaged with the rack. The crown gear is mounted in the handle in meshed engagement with the motor gear. The potentiometer is coupled to the crown gear. The control system is electrically coupled to the trigger, the electric motor, and the potentiometer.

In certain embodiments, a handle assembly for a surgical stapler is provided. The handle assembly comprises a handle body, a power system, an actuation shaft, and an articulation mechanism. The handle body comprises a stationary handle and a trigger pivotably coupled to the handle body. The power system is within the handle body. The actuation shaft is operatively coupled to the power system. The actuation shaft is slidable within the handle body along a longitudinal axis. The articulation mechanism comprises a manually actuated articulation knob and an articulation adapter. The manually actuated articulation knob is positioned at a proximal end of the handle body and rotatable about the longitudinal axis. The articulation adapter is positioned at the distal end of the handle body. The articulation adapter is operatively coupled to the articulation knob such that rotation of the articulation knob about the longitudinal axis longitudinally slides the articulation adapter.

DETAILED DESCRIPTION OF THE INVENTION

Figure 1:
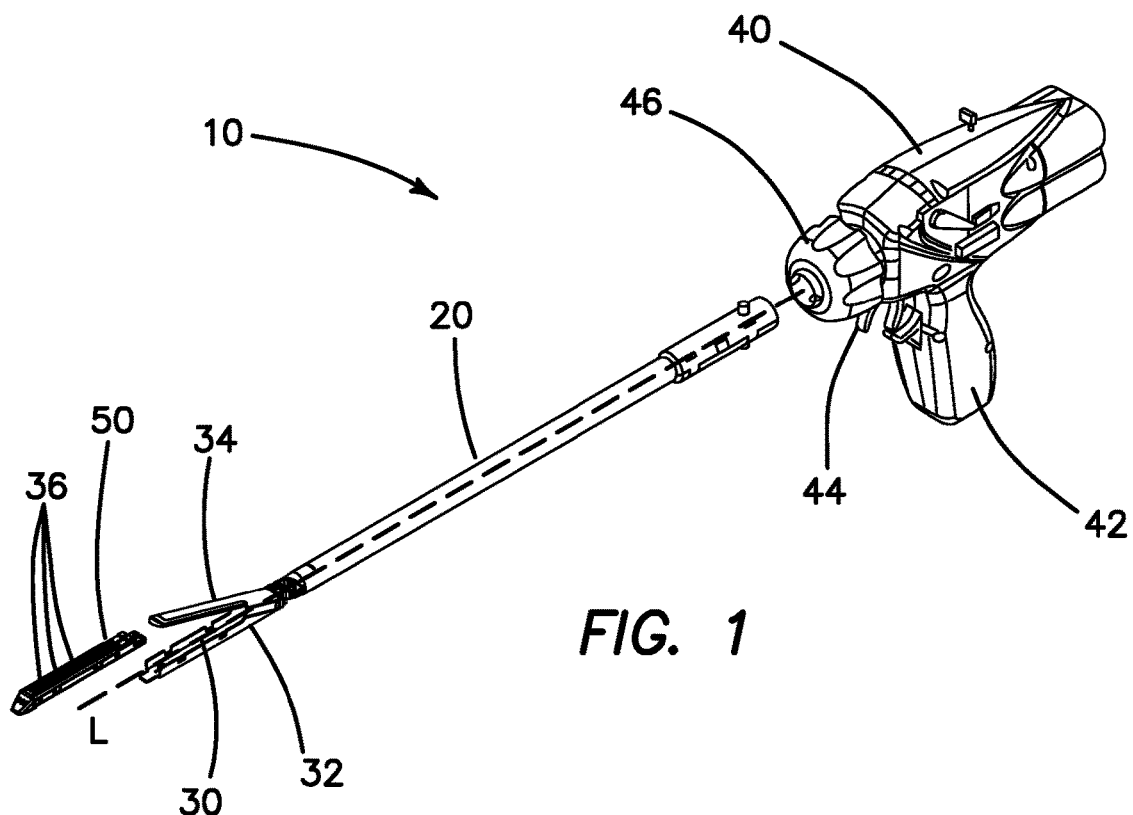
FIG. 1 is a perspective view of an embodiment of surgical stapling system having an embodiment of powered handle.
Figure 2:
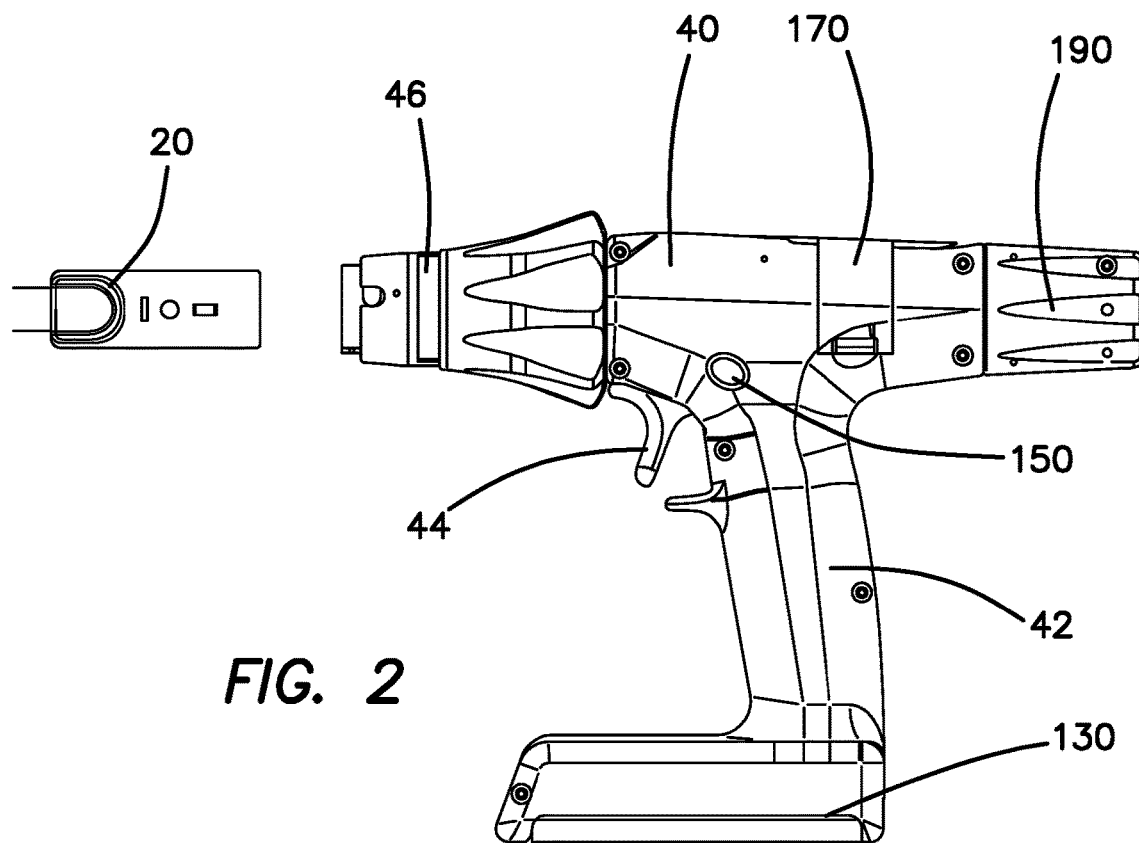
FIG. 2 is a side view of another embodiment of powered handle for the surgical stapling system of FIG. 1.

With reference to FIGS. 1-2, an embodiment of surgical stapling system is illustrated. The illustrated embodiment of surgical stapler 10 comprises an elongate shaft 20, a jaw assembly 30, and a handle assembly 40. FIG. 1 illustrates the surgical stapler 10 with the jaw assembly 30 in an open configuration with an embodiment of powered handle having powered staple firing and powered jaw assembly articulation. FIG. 2 illustrates another embodiment of a powered handle 40 of the surgical stapler system 10 with the elongate shaft removed. The powered handle 40 of FIG. 2 has powered staple firing and manual jaw assembly articulation. In the illustrated embodiments, the shaft 20 and jaw assembly 30 can be freely rotated about a longitudinal axis defined by the shaft 20 by rotation of a rotation knob on the handle 40. In other embodiments, the stapling system can be configured to allow rotation of the jaw assembly about the longitudinal axis within a predefined range or a rotationally fixed jaw assembly.

With continued reference to FIG. 1, the illustrated embodiment of surgical stapler 10 can be sized and configured for use in laparoscopic surgical procedures. For example, the elongate shaft 20 and jaw assembly 30 can be sized and configured to be introduced into a surgical field through an access port or trocar cannula. In some embodiments, the elongate shaft 20 and jaw assembly 30 can be sized and configured to be inserted through a trocar cannula having a relatively small working channel diameter, such as, for example, less than 8 mm. In other embodiments, elongate shaft 20 and jaw assembly 30 can be sized and configured to be inserted through a trocar cannula having a larger working channel diameter, such as, for example, 10 mm, 11 mm, 12 mm, or 15 mm. In other embodiments, it is contemplated that certain aspects of the surgical staplers described herein can be incorporated into a surgical stapling device for use in open surgical procedures.

With continued reference to FIG. 1, as illustrated, the elongate shaft 20 comprises a generally tubular member. The elongate shaft 20 extends from a proximal end to a distal end. The elongate shaft 20 defines a central longitudinal axis, L. of the surgical stapler 10 extending between the proximal end 22 and the distal end 24.

With continued reference to FIG. 1, in the illustrated embodiment, the jaw assembly 30 is coupled to the elongate shaft 20 at the distal end of the elongate shaft 20. The jaw assembly 30 comprises a first jaw 32 and a second jaw 34 pivotally coupled to the first jaw 32. In the illustrated embodiment, the first jaw 32 is fixed to the distal end 24 of elongate shaft 20 such that it extends distally along the central longitudinal axis, L and is articulable with respect to the elongate shaft 20 responsive to an articulation mechanism in the handle 40. In an initial configuration, the first jaw 32 includes a plurality of staples 36 disposed therein within a reload 50. In other embodiments, the reload 50 can be integrated with the jaw assembly 30 such that the entire shaft assembly 20 and jaw assembly 30 with loaded staples define a single reload assembly. In some embodiments, staples can be initially positioned in the second jaw 34.

With continued reference to FIG. 1, in the illustrated embodiment, the jaw assembly 30 can be actuated from an open configuration (FIG. 1) to a closed configuration to a stapling configuration by an drive member or beam that is longitudinally slideable within the elongate shaft. In an initial position, the beam can be positioned at the distal end 24 of the elongate shaft 20. With the beam in the initial position, the second jaw 34 is pivoted away from the first jaw 32 such that the jaw assembly 30 is in the open configuration. The actuation beam engages the second jaw 34 upon translation of the actuation member or beam distally along the longitudinal axis L. Translation of the actuation beam distally from the initial position a first distance can actuate the jaw assembly from the open configuration to the closed configuration. With the jaw assembly 30 in the closed configuration, the actuation beam can be returned proximally the first distance to return the jaw assembly 30 to the open configuration. A distal end of the actuation beam can advance a staple slider configured to deploy staples from the first jaw 32 such that further translation of the actuation beam distally past the first distance deploys the plurality of staples 36 from the reload 50 in the first jaw 32.

With continued reference to FIG. 1, in the illustrated embodiment, the handle assembly is coupled to the elongate shaft 20 at the proximal end of the elongate shaft 20. As illustrated, the handle assembly 40 has a pistol grip configuration with a housing defining a stationary handle 42 and a movable handle 44 or trigger pivotably coupled to the stationary handle 42. It is contemplated that in other embodiments, surgical stapler devices including aspects described herein can have handle assemblies with other configurations such as, for example, scissors-grip configurations, or in-line configurations. As further described in greater detail below, the handle assembly 40 houses a powered actuation mechanism configured to selectively advance an actuation shaft responsive to movement of the movable handle 44.

In the illustrated embodiment, the surgical stapler 10 can include the plurality of staples 36 positioned in a disposable cartridge reload 50 while the jaw assembly 30 is configured to be reused with multiple staple cartridge reloads 50 in a single procedure. In the some embodiments, the elongate shaft 20 and jaw assembly 30 define a disposable reload shaft that is removably couplable to the handle assembly 40. Accordingly, in the illustrated embodiment the handle assembly 40 includes a coupler 46 at the distal end thereof. The coupler 46 is adapted to engage the elongate shaft 20 of the surgical stapler 10 The coupler 46 can have a bayonet connection having an outer connector that can removably couple to handle assembly 42 the elongate shaft 20, and an inner connector that can removably couple the actuation shaft of the handle assembly 42 to the drive member of the elongate shaft 20. Accordingly, the surgical stapler 10 can be configured such that the handle assembly 40 can be reused with multiple reload shafts 20 during a surgical procedure. It is contemplated that in other embodiments, the handle assembly and some portion of the elongate shaft can be reusable while a remainder of the elongate shaft in the jaw assembly define a disposable cartridge. In certain other embodiments, the handle assembly and the elongate shaft can be reusable while the jaw assembly defines a disposable cartridge. In still other embodiments, a jaw insert housing a plurality of staples can define a disposable cartridge while the remainder of the surgical stapler is reusable.

With reference to FIG. 2, an embodiment of powered handle for a surgical stapling system is illustrated. The powered handle can be used with various shaft reloads and cartridges such that the shaft configuration, jaw assembly configuration, and staple configuration can be selected for a particular procedure. The illustrated embodiment of handle provides powered (motor-driven) clamping and opening of the jaws and firing of the staple line. Articulation of the jaw assembly can be manually controlled by an articulation knob that the operator rotates. The motor is controlled by an embedded control system that dictates functionality of the handle during different stages of use.

With continued reference to FIG. 2, the powered handle 40 comprises a pistol-grip configuration with a stationary handle 42 and a movable handle 44 or trigger pivotably coupled thereto. A power supply 130 or battery can be positioned on a lower surface of the stationary handle. The powered handle 40 can further comprise a user control such as a fire or fire/reverse button 150 to allow a user to selectively control a stapling sequence. The powered handle 40 can further comprise a redundant, manual return system 170 to allow a user to manually return the stapling system to an open configuration in the event of a powered system failure, control system failure, power supply failure, or "lockjaw" or other mechanical binding. The powered handle can further comprise a manual articulation mechanism including a rotatable articulation knob 190. In the illustrated embodiment, the articulation knob 190 is positioned on the proximal end of the powered handle and is rotatable about an axis generally corresponding to the longitudinal axis of the stapling system.

Figure 2A:
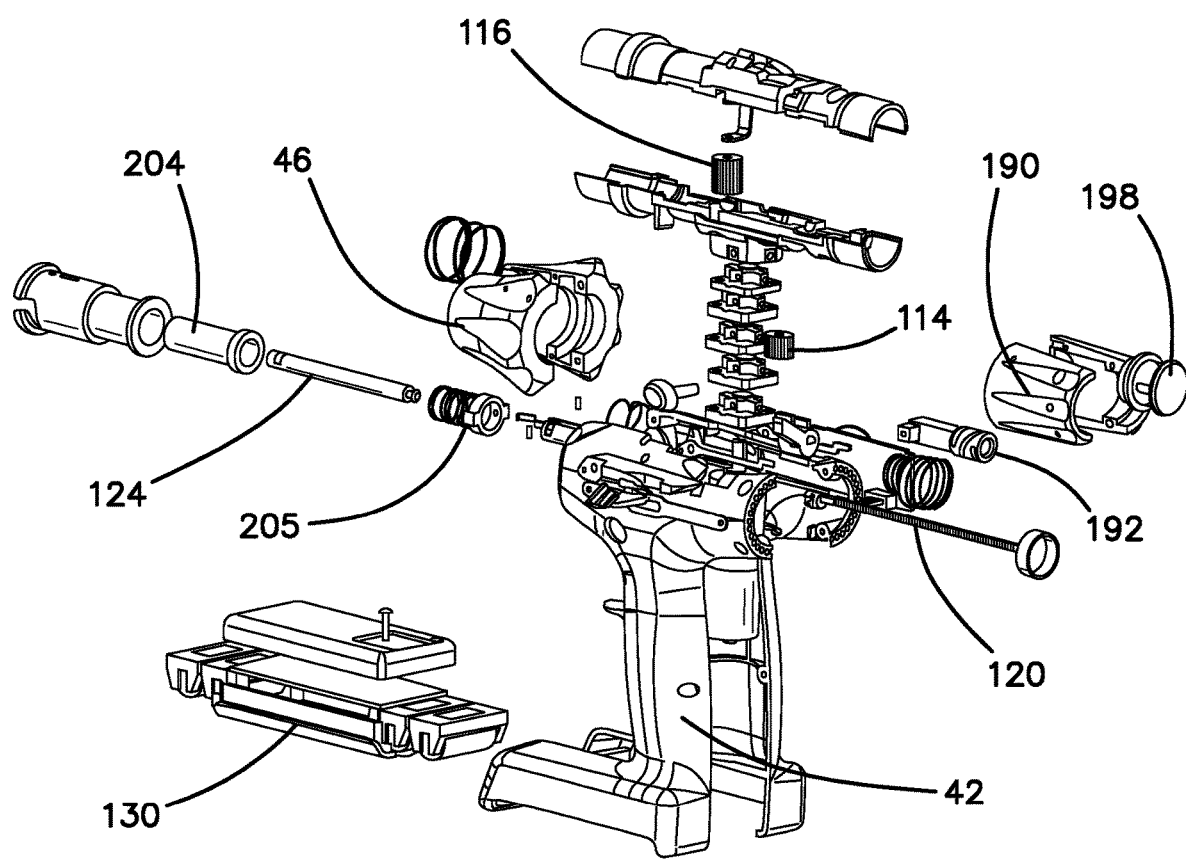
FIG. 2A is an exploded perspective view of the powered handle for the surgical stapling system of FIG. 2.

With reference to FIG. 2A, the powered handle of FIG. 2 is illustrated in an exploded assembly view. Various elements of the illustrated embodiment of powered handle further discussed herein are identified in the exploded assembly view.

Figure 3:
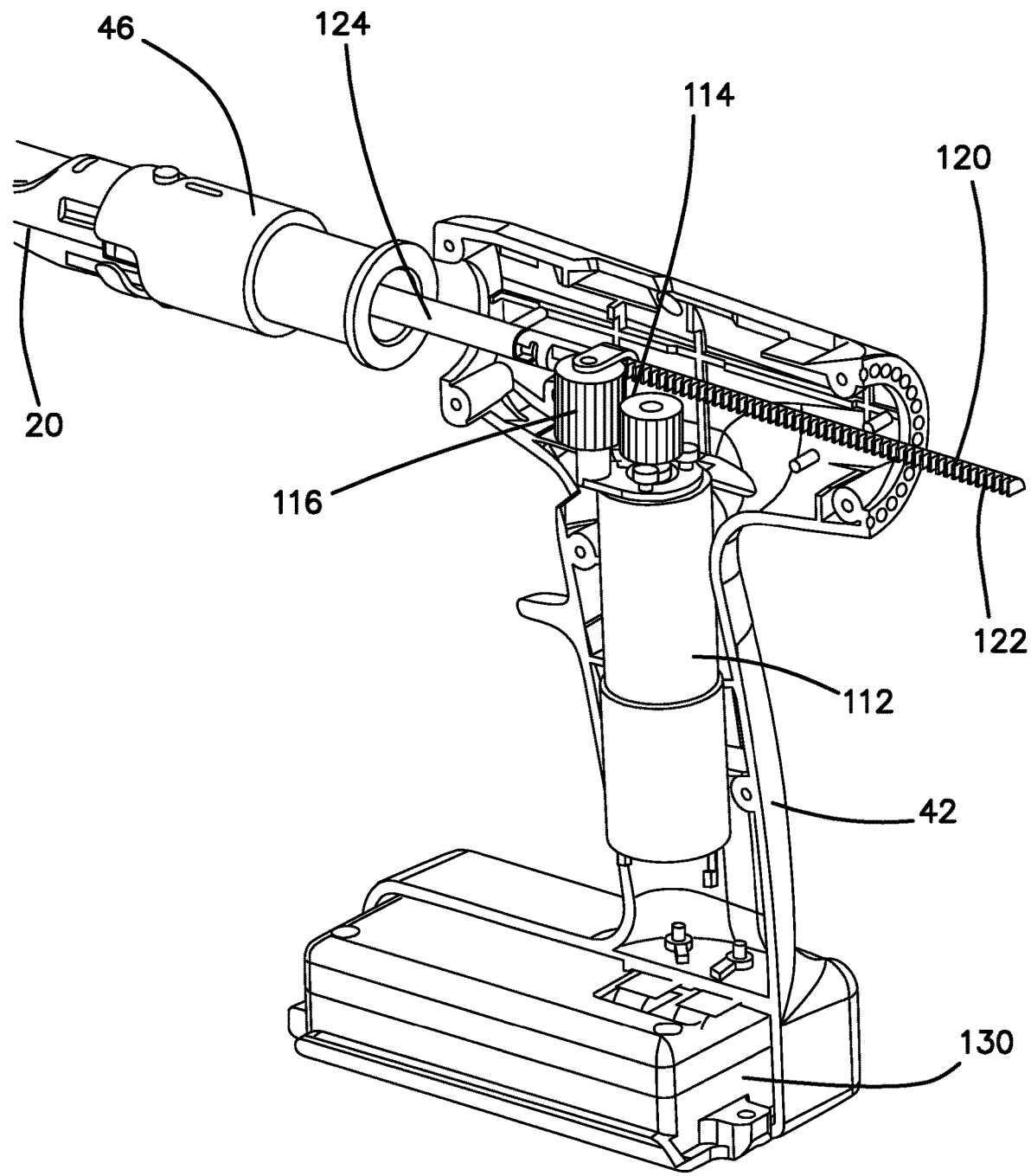
FIG. 3 is a partial cutaway perspective view of the powered handle of FIG. 2 with components removed to illustrate a drive system thereof.

With reference to FIG. 3, a partial cut-away view of the powered handle is illustrated with a shaft 20 positioned in the coupler 46 of the handle. In the illustrated cut-away view, several components of the powered handle have been removed to clearly depict a drive system of the powered handle. In the illustrated embodiment, the drive system comprises a motor 112 positioned within the stationary handle 42, a motor gear 114 positioned on an output shaft of the motor 112, and an auxiliary gear 116 in driven engagement with the motor gear 114. In some embodiments, the motor 112 is a brushed DC gearmotor. Advantageously, transmitting power through the auxiliary gear 116 can allow the motor 112 to be laterally centered within the stationary handle to enhance handle balance and user ergonomics. Furthermore, in some embodiments, the motor gear 114 and auxiliary gear 116 can be configured to provide a desired operational torque at the rack 122. In some embodiments, the motor 112 can include a multigear transmission operationally coupled between the motor 112 and the motor gear 114 coupled to the auxiliary gear 116 to provide the desired operational torque. The motor 112 can be electrically coupled to the power supply 130 via a control system. The control system within the handle interfaces with the drive system to measure the position of the actuation shaft 120 and therefore the actuation of the jaw assembly.

The drive system is mounted to hardware that provides information to a control system including a microprocessor within the handle. This embedded system can control the speed and torque of the motor. It can also control functionality of the device based on user inputs (movement of the trigger and pressing of the FIRE/REVERSE button) and position of the drive system. The control system also can measure feedback from the motor to determine whether loads are too high to continue firing staples, or whether a reload cartridge lockout has been activated. It will also measure battery life and can limit the number of firings of the device.

Figure 20:
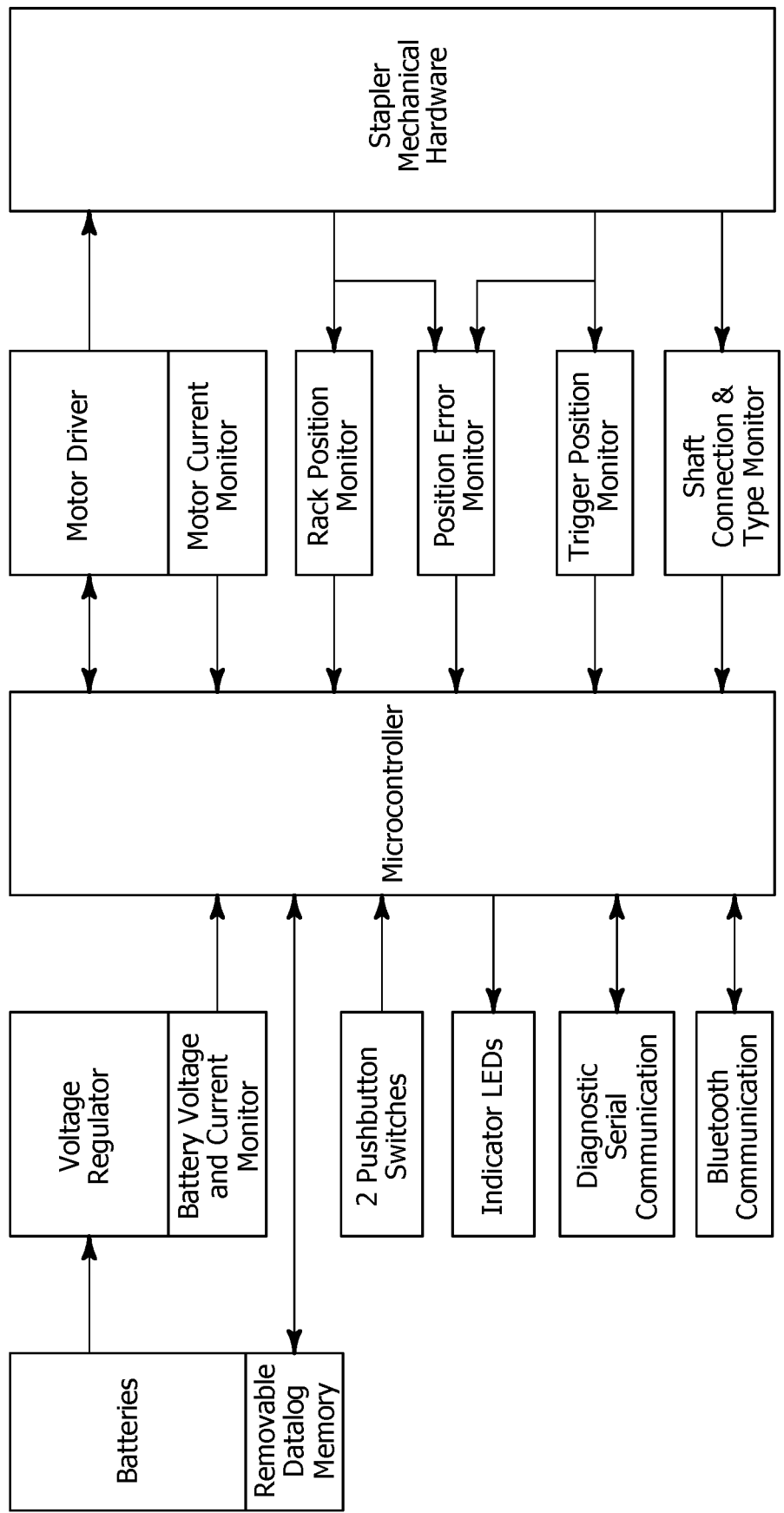
FIG. 20 is a schematic diagram of information and power flow for an embodiment of control system for the powered handle of FIG. 2.

With respect to FIG. 20, a schematic flow diagram indicating data and power flow for an exemplary control system for a powered handle is illustrated. In the illustrated flow diagram, the control system comprises the illustrated microcontroller. In various embodiments, the microcontroller can comprise an application specific integrated circuit or a general purpose microprocessor running application specific firmware and/or software. As illustrated, the microcontroller receives power and data regarding battery status from the batteries in the power supply. The microcontroller further receives data from various mechanical hardware of the stapler such as a motor driver and current monitor, an actuation rack position sensing mechanism, and a shaft connection and type monitor. The microcontroller further receives data from a user via a trigger position sensor, pushbutton switches, and a bluetooth communications transceiver. The control system can output a control signal to actuate the drive system of the powered handle through a motor driver. The control system can also output certain operational parameter information to a memory module on the power supply, and can output certain data for user viewing through LED lights on the handle and the bluetooth communications transceiver.

In certain embodiments, the control system is also configured to further define operational parameters of the powered handle. For example, by querying a memory module on the power supply or on the control system itself, the control system can detect whether the powered handle has been used for more than a single procedure. In some embodiments, the stapling system is designed for use in a single procedure and is not designed for resterilization. Additionally, the control system can also query the memory modules on the power supply or the control system to detect a number of staple firings to assess whether sufficient battery power remains to complete an additional firing.

In certain embodiments, the control system is configured to detect tissue characteristics that can prevent staple firing. In some embodiments, the control system can monitor position, velocity, and supplied torque of the motor in the drive system. The control system can detect whether excessive torque is required to close the jaw assembly, if excess time is needed to close the jaw assembly, or if the jaws are closing at a low speed. These conditions may indicate that the tissue in the jaw assembly is too thick or too dense for the stapler to be effective. In certain embodiments, the control system can monitor the position of the actuation shaft with respect to time and evaluate this monitored position and time with respect to a baseline 'zero load' time reference position and time to assess the tissue characteristics such as thickness and density. In instances where the drive system exceeds predetermined operational parameters, the control system can indicate an error condition and stop a firing operation.

In some embodiments, the control system can provide user information over a bluetooth connection. The powered handle can include a low-power bluetooth transceiver to allow data regarding operational parameters such as battery status, number of remaining filings, and estimated tissue thickness to be displayed unobtrusively on a bluetooth-connected display.

Figure 21:
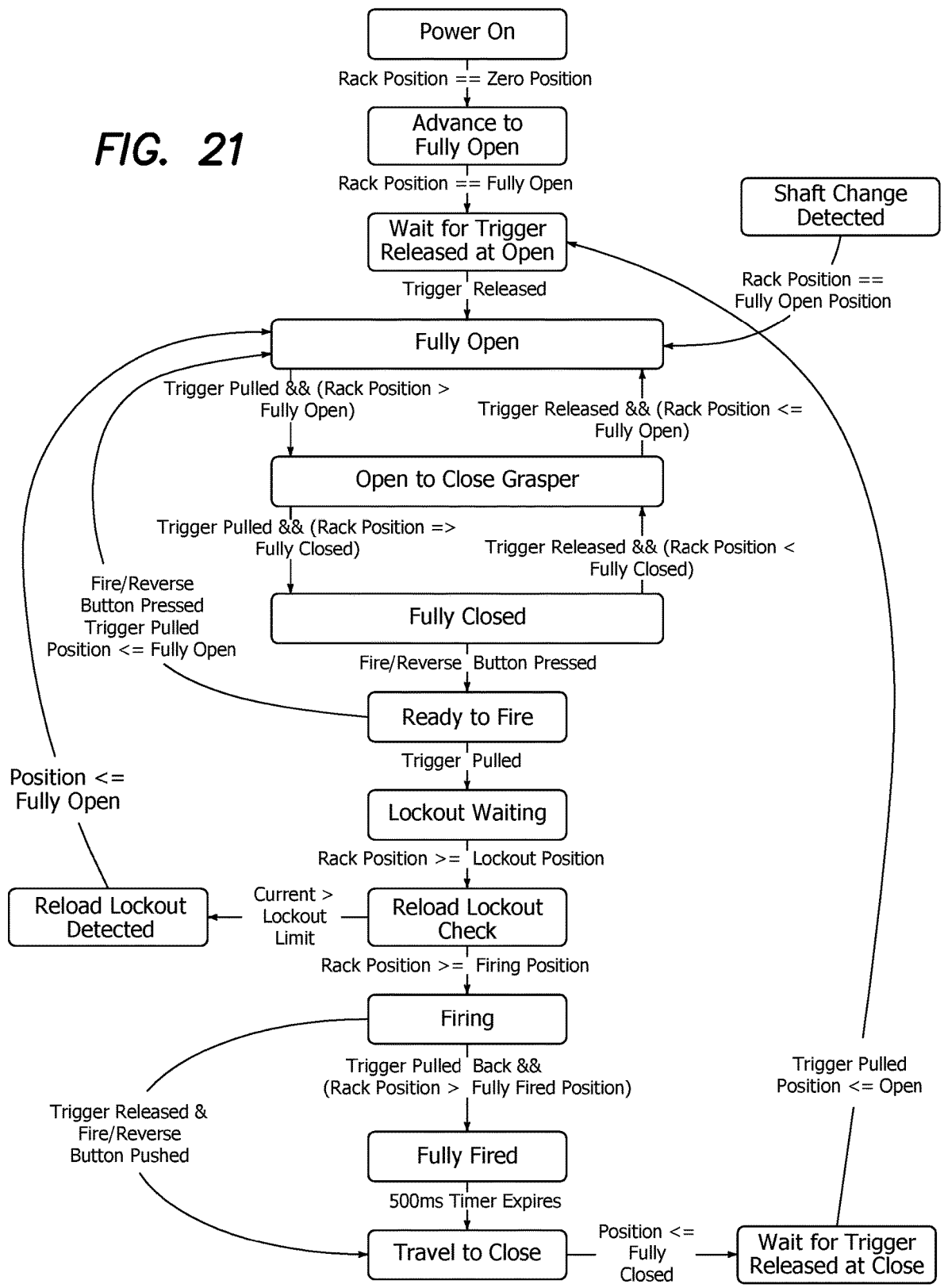
FIG. 21 is an operational sequence flow chart for an exemplary operational sequence of the powered handle of FIG. 2.

With reference to FIG. 21, a schematic of an operational flow chart for an exemplary firing sequence of the control system is illustrated. As illustrated, the control system integrates user inputs from the trigger and firing button as well as hardware inputs from various sensors and monitors to advance the jaw assembly from a fully open condition to a fully closed condition to a firing sequence, then back to the fully open condition.

Figure 4:
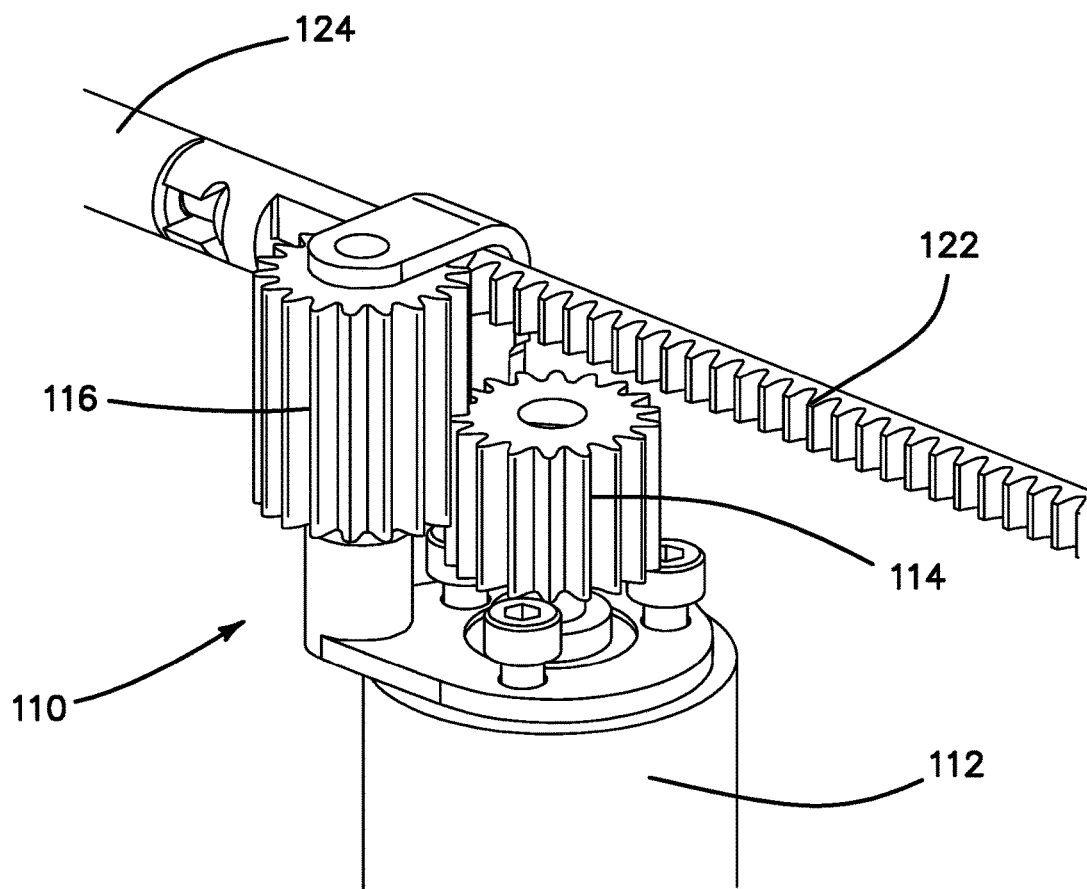
FIG. 4 is a perspective view of an embodiment of drive system for the powered handle of FIG. 2.
Figure 5:
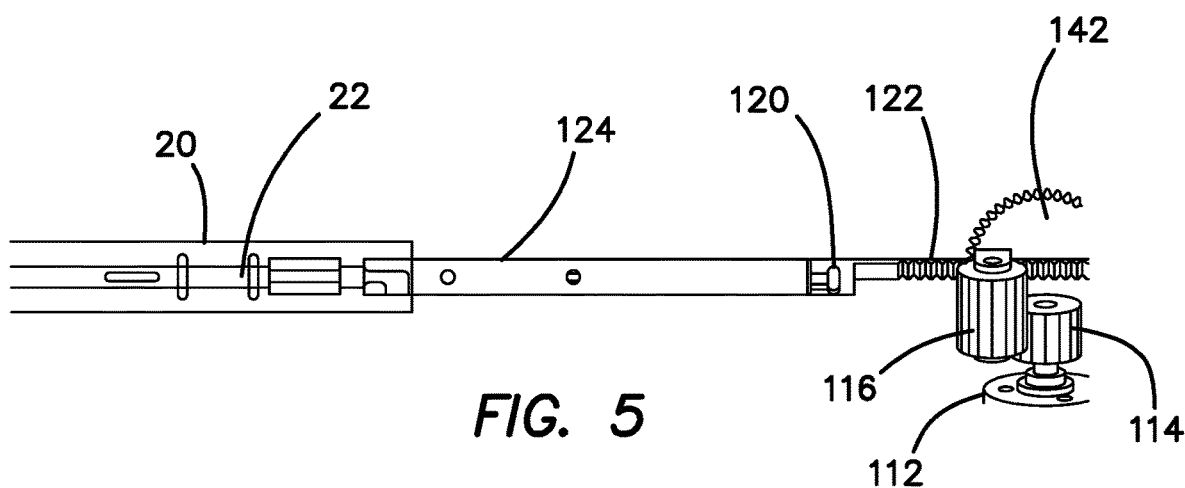
FIG. 5 is a side view of an embodiment of drive system for the powered handle of FIG. 2.

With reference to FIGS. 3-5, during powered operation, the auxiliary gear 116 is in meshed engagement with a rack 122 on an actuation shaft 120 extending longitudinally within the handle body. In the illustrated embodiment, the auxiliary gear is supported in a guide member through which the actuation shaft 120 slides. The guide member assists in maintaining meshed contact between the auxiliary gear and the rack 122. A distal end of the actuation shaft 120 is freely rotatably coupled to an actuation adapter 124 that extends longitudinally into the coupler 46 at the distal end of the powered handle.

With the shaft 20 coupled to the coupler 46 of the powered handle 40, the actuation adapter 124 connects to a drive member in the shaft 20 via a bayonet connection. Therefore, when the shaft 20 is attached to the handle 40, the motor 112 and rack 122 will drive a drive member 22 coupled to the jaw assembly. Thus, the drive system within the handle comprises a "rack and pinion" design. Operation of the motor 112 responsive to a user's input will drive the actuation shaft 120 longitudinally forward and reverse to selectively actuate the stapler in closing, firing, or opening operations.

Figure 6:
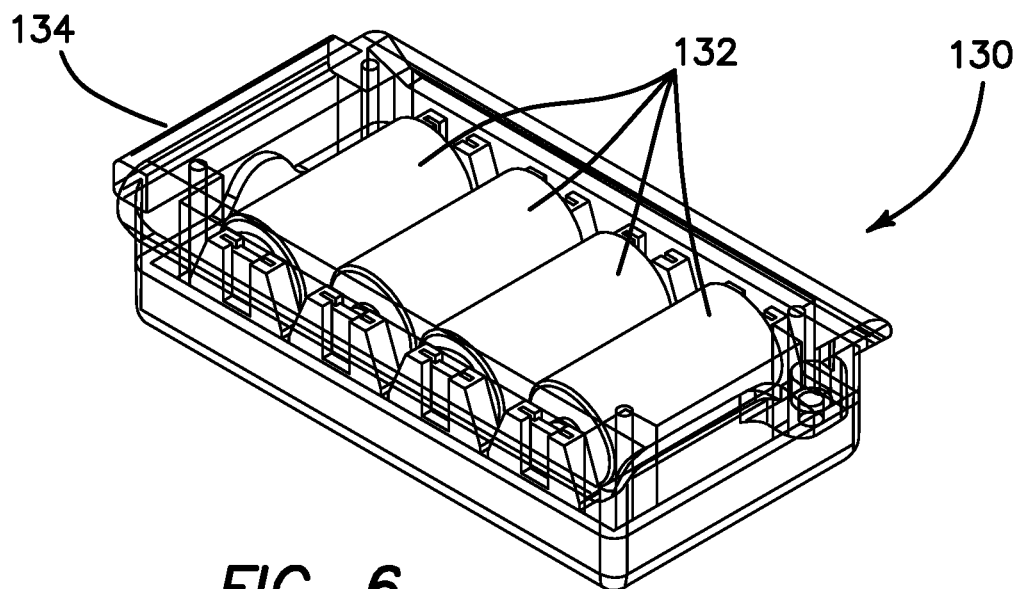
FIG. 6 is a perspective view of an embodiment of power supply for the powered handle of FIG. 2.
Figure 7:
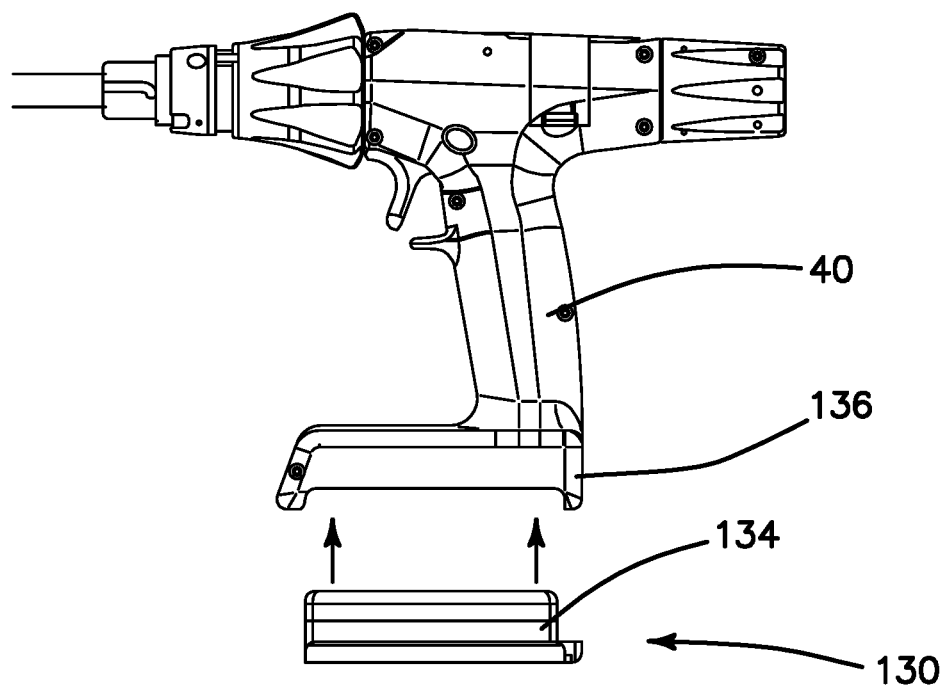
FIG. 7 is a side view of the powered handle of FIG. 2 with the power supply in position for installation.

With reference to FIGS. 6 and 7, an embodiment of power supply 130 for the powered handle 40 is illustrated. The power supply 130 can be configured to deliver direct current to the powered handle motor and control system. In the illustrated embodiment, the stapler can operate at 12 V. The illustrated power supply can comprise four 3V lithium-ion batteries 132 connected in series to produce a 12V power supply. As illustrated, the batteries 132 are stacked in a 4 by 1 configuration in a plastic housing 134 to form the battery pack. In other embodiments, other numbers and configurations of individual battery cells can be used to form the battery pack. For example, in certain embodiments, the battery pack can be comprised of AA, AAA, or another standard or purpose-built single use or rechargeable chemistry battery. In the illustrated embodiment of powered handle 40, the battery pack is located at the bottom of the stationary handle. Desirably, this positioning provides a stable surface to set the handle 40 on a flat surface. It is contemplated that in other embodiments, the power supply can be positioned elsewhere in the handle, such as at a proximal end thereof (see, for example, the embodiment of FIG. 1).

With continued reference to FIGS. 6 and 7, in some embodiments, the power supply 130 can be packaged with the handle 40 but will not be installed before use. At the time of use, the user can install the battery pack by inserting it into a battery cavity 136 located at the bottom of the handle 40. Advantageously, shipping the battery pack uninstalled can reduce an incidence of accidental battery discharge before use. Moreover, a removable battery pack can allow the stapler system be easily upgraded with a new battery as new battery technology becomes available. In other embodiments, the power supply can be packaged installed in the handle with a removable strip blocking electrical connection of the battery pack. In still other embodiments, the handle can be supplied with a power cable configured to be plugged into an AC or DC power source such as a wall socket, a USB connector, or another standard electrical connection.

In some embodiments, the power source further comprises a memory module such as a non-volatile memory that can store a digital record of the usage of the stapler. For example, the memory module can be configured to record details of each firing of the stapler including a periodic sampling of the battery voltage and motor current during firing, the sequence of states of the software state machine, any unexpected events that may have occurred, the shaft types that were used, the number of firings, the intervals between firings, and the model and serial number of the stapler handle. It can also record if the battery pack itself has been used so that users cannot reuse the battery pack.

In some embodiments, the powered handle 40 and associated power supply 130 can be configured for use in a single procedure and disposal following the procedure. The power supply 130 can include a power drain to reduce an opportunity for reuse. Following use in a surgical procedure, a user can remove the battery pack from the handle 40. Removing the battery pack from the handle 40 can initiate draining the batteries. For example, after the battery pack has been used once a mechanical feature that can short circuit the battery by connecting the terminals to a low value resistor or an electrical feature can accomplish the same task with a circuit. Additionally, if the battery pack is left in the handle 40 after the surgical procedure is complete, in some embodiments, the control system of the handle is programmed to disable functionality and drain the battery pack after a maximum time limit.

Figure 8:
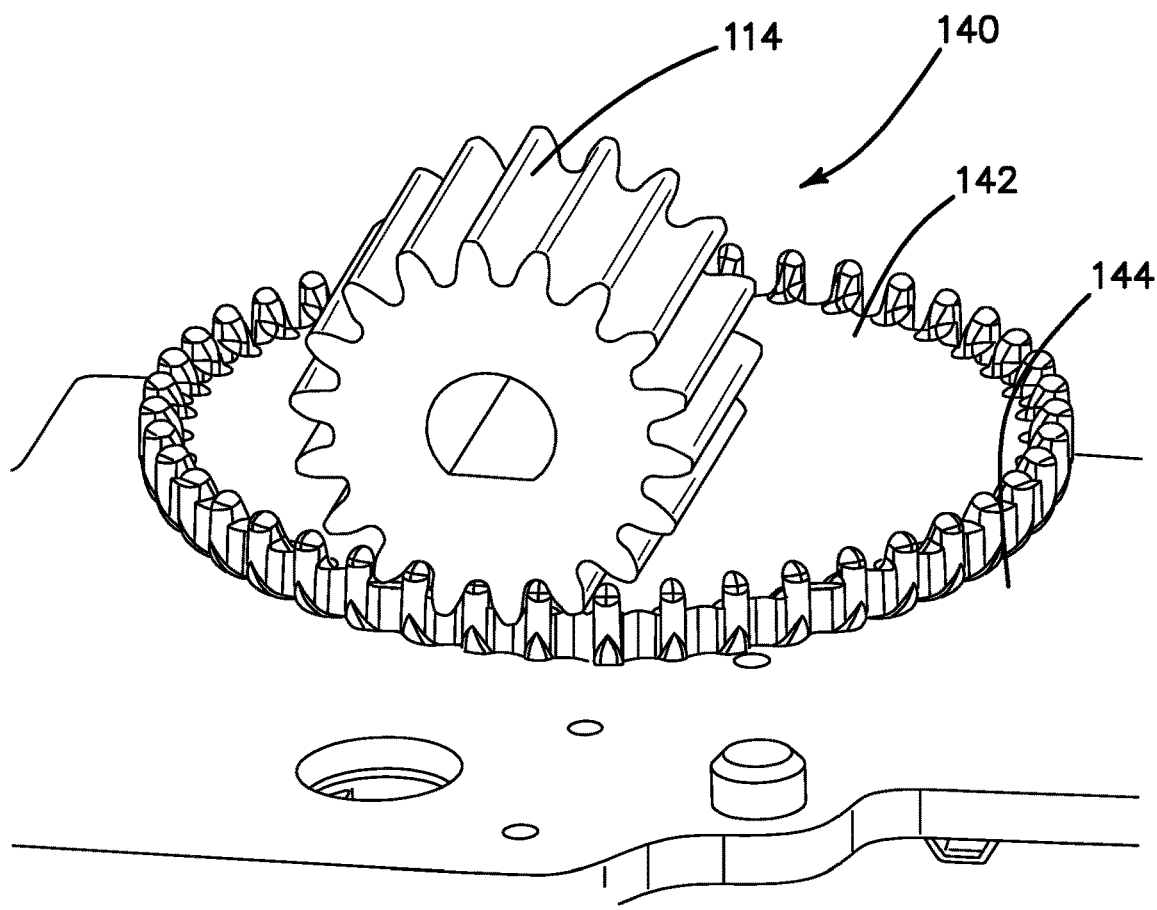
FIG. 8 is a perspective view of an embodiment of position indexing system for the powered handle of FIG. 2.

With reference to FIGS. 2 and 8, an embodiment of position sensor mechanism for use in the powered handle is illustrated. In operation, rotation of the motor gear 114 correspondingly rotates a crown gear 142 mounted in the handle 40. The crown gear 142 is coupled to a potentiometer such the position of the motor gear 114 and thus the actual position of the actuation rack can be determined based on the measuring changes in resistance at the potentiometer. In some embodiments, the potentiometer can be mounted on a circuit board 144 on which the control system can be positioned. While the illustrated embodiment includes a potentiometer-based position sensor mechanism, it is contemplated that in other embodiments, other position sensing mechanisms can be used, including, for example, use of a magnetic encoder with hall effect sensors, use of limit switches that activate when the actuation shaft has traveled a predetermined distance, use of optical systems such as photodiodes to measure travel of a pattern along the actuation shaft, or other position sensing systems.

With reference to FIG. 9A-9D, an operation sequence of engagement of a stapler shaft 20 with the coupler 46 of the handle is illustrated. In the illustrated embodiment, the reload shaft 20 to handle 40 connection comprises a bayonet style connection, in which a user axially aligns and inserts the reload shaft 20 into the handle 40 and rotates the reload shaft 20 approximately 90 degrees to connect. This bayonet connection operatively couples two mechanical functions of the reload shaft 20 to corresponding actuators of the handle 40. When the bayonet connection is fully coupled, an articulation member within the shaft 20 is coupled to an articulation adapter of the handle and a drive member within the shaft 20 is coupled to the actuation adapter. Furthermore, the handle 40 and shaft 20 can be configured with a latch mechanism at the coupler 46 to prevent a user from removing the shaft 20 once the actuation adapter and drive member has been activated. Moreover, the connection at the coupler 46 can include a reload identifying mechanism such that the control system of the handle can detect if a reload shaft is connected, and if so what the attached jaw length of the reload is. It is contemplated that the powered handle can be used with reload shafts 20 including different length jaw assemblies. For example, in some embodiments the same handle 40 can be used with either 45 mm or 60 mm length jaw assemblies. Thus, if the jaw assembly length is identified by the control system of the powered handle, the control system can direct a motor actuation profile for a firing stroke of the stapler corresponding to the identified length of the jaw assembly.

Figure 9A:
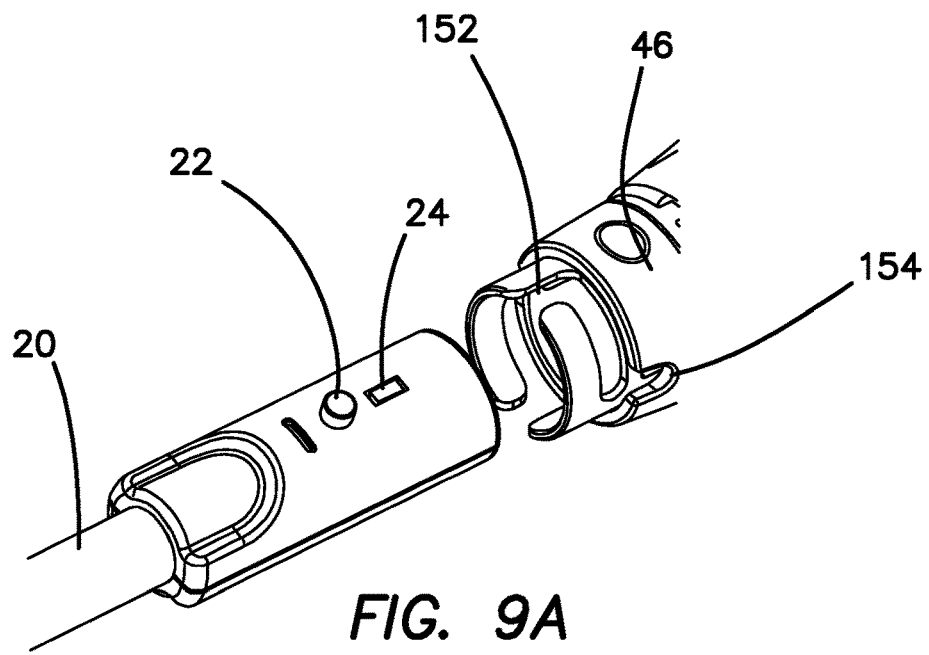
FIG. 9A is a perspective view of an embodiment of shaft coupler for the powered handle of FIG. 2 with an embodiment of shaft in a removed position.

In FIG. 9A, the shaft 20 is positioned in alignment with the coupler 46 on the handle, and a release knob of the coupler 46 is withdrawn to expose a bayonet channel 152 of the coupler 46 on a rotation insert of the coupler 46. The shaft 20 can include a retention post 22 or boss positionable within the bayonet channel 152. In the illustrated embodiment, the shaft includes two bosses positioned 180 degrees apart on the outer surface thereof and the coupler 46 includes a corresponding two bayonet channels 152. It is contemplated that in other embodiments, other numbers and configurations of bosses and bayonet channels can be used to provide a desired connection strength and ease of alignment.

Figure 9B:
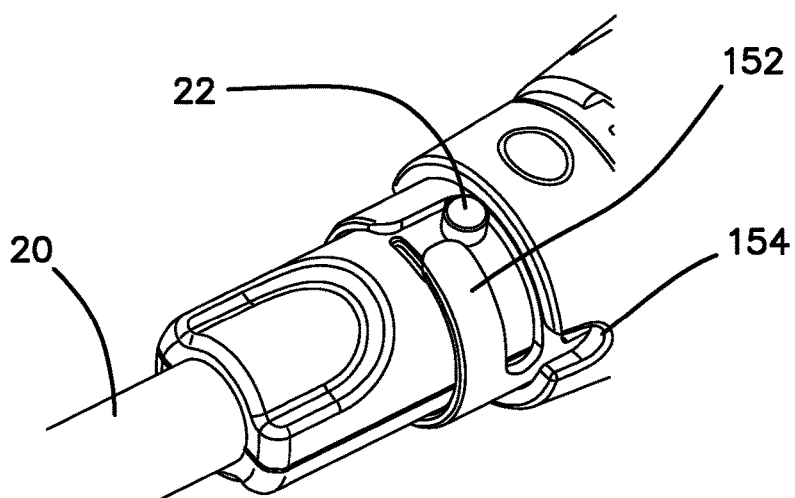
FIG. 9B is a perspective view of an embodiment of shaft coupler for the powered handle of FIG. 2 with an embodiment of shaft in a partially inserted position.
Figure 9C:
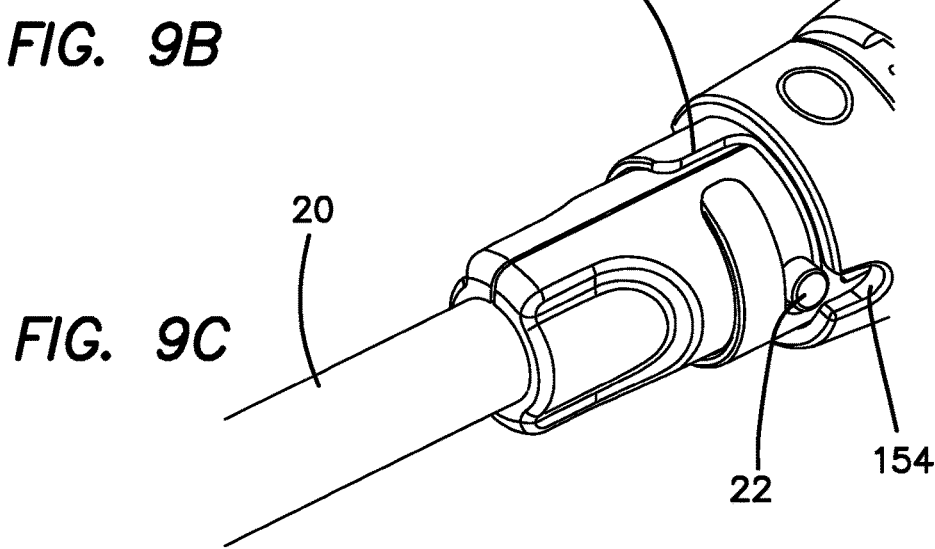
FIG. 9C is a perspective view of an embodiment of shaft coupler for the powered handle of FIG. 2 with an embodiment of shaft in a fully inserted position.
Figure 9D:
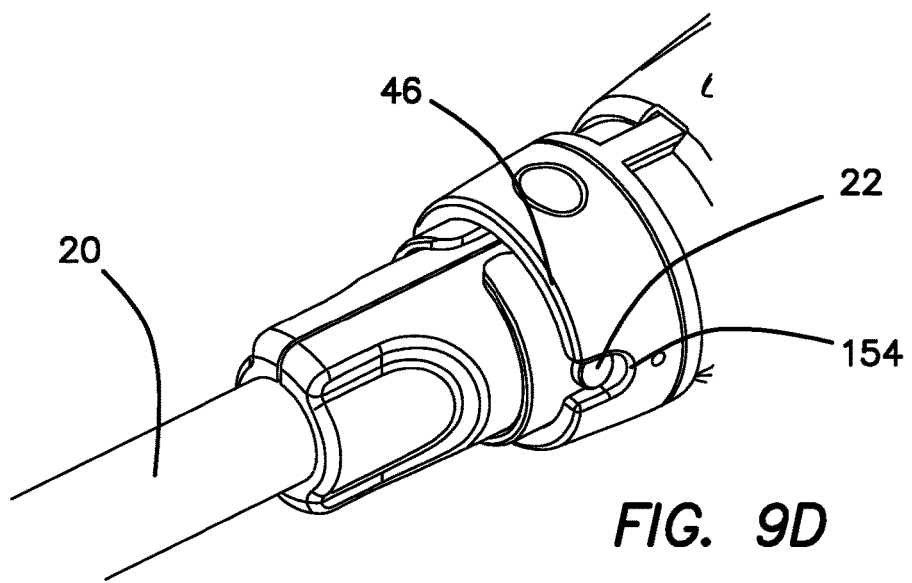
FIG. 9D is a perspective view of an embodiment of shaft coupler for the powered handle of FIG. 2 with an embodiment of shaft in a retained position.

With reference to FIG. 9B, the retention post 22 of the shaft is positioned within the bayonet channel 152. With reference to FIG. 9C, the reload shaft 20 has been rotated 90 degrees relative to the handle such that the retention post 22 of the shaft has reached a connected end of the bayonet channel 152. With reference to FIG. 9D, the release knob of the coupler is released to allow a retention recess 154 on the release knob to retain the retention post 22 of the reload shaft 20.

Figure 10A:
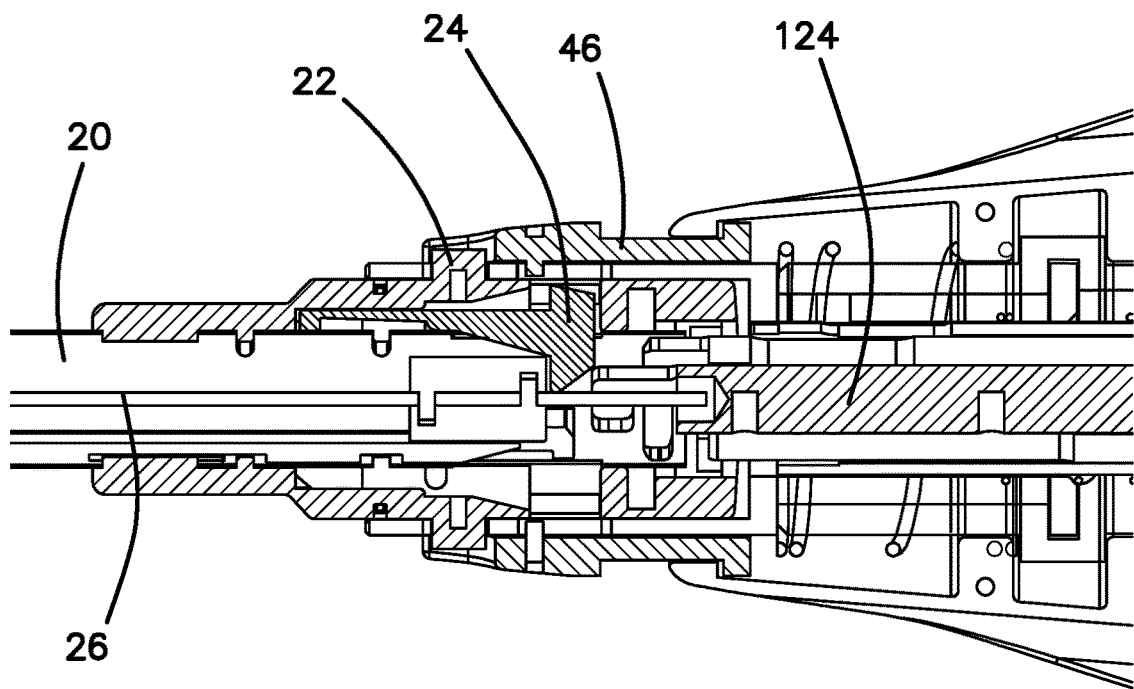
FIG. 10A is a cut-away side view of an embodiment of shaft coupler of FIG. 2 with an embodiment of shaft in a retained position.
Figure 10B:
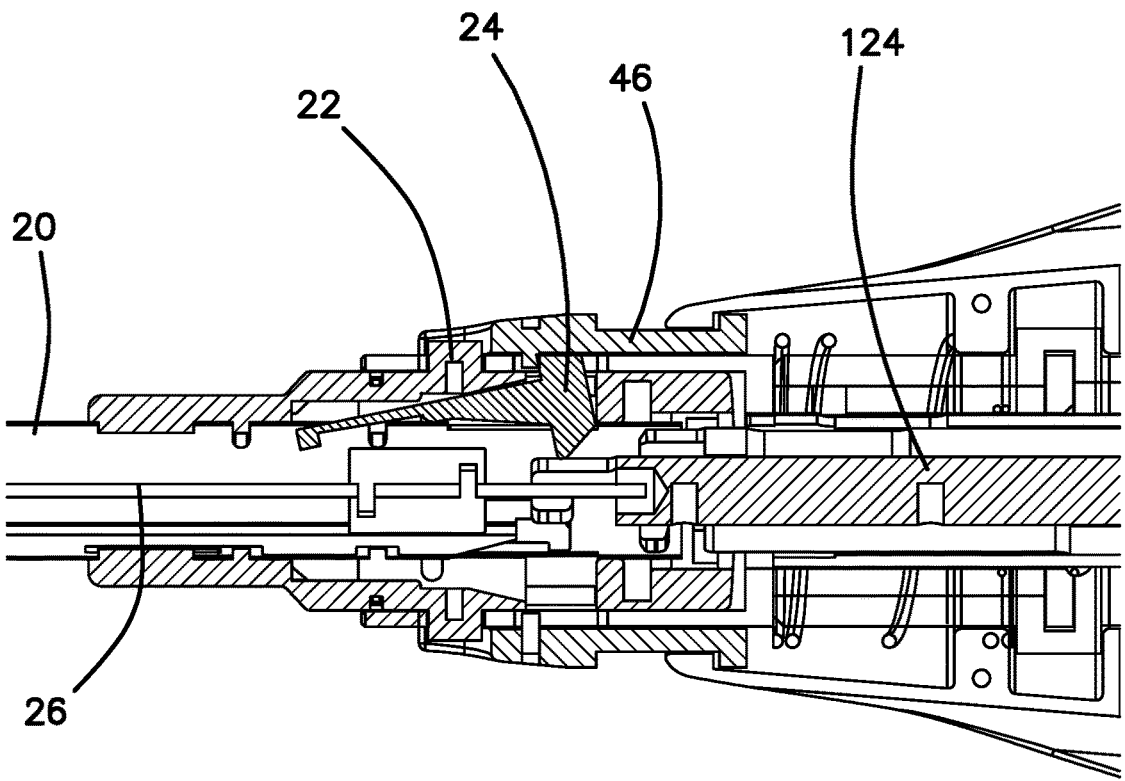
FIG. 10B is a cut-away side view of an embodiment of shaft coupler of FIG. 2 with an embodiment of shaft in a latched position.

With reference to FIGS. 10A-10B, a cut-away side view of the coupler 46 with a reload shaft 20 is illustrated. The retention post 22 of the shaft is positioned within the retention recess of the bayonet channel. The actuation adapter 124 is coupled with a drive member 26 extending longitudinally within the shaft 20. FIG. 10B illustrates a lock-in or retention mechanism that operates upon initial distal advancement of the actuation adapter 124. As illustrated, a locking member 24 is pivotably coupled to a proximal end of the shaft 20.

With continued reference to FIG. 10B, the locking member 24 can include a ramped or tapered lock surface at a proximal edge thereof. As illustrated in FIG. 10A, the shaft 20 is in a coupled, but unlocked configuration with respect to the coupler 46. In the coupled, unlocked configuration, the shaft 20 can be removed from the coupler 46 through the bayonet connection by a reverse of the sequence of operations of FIGS. 9A-9D. Once the actuation adapter 124 is advancing to operate the stapler, the actuation adapter 124 interacts with the ramped surface of the locking member 24 to advance the locking member radially outward into a locked position. In the locked position (FIG. 10B), the locking member 24 engages a locking ledge on the coupler 46 to lock in the shaft. With the shaft 20 locked in with respect to the handle 40, the shaft 20 cannot be removed from the handle 40 until the actuation adapter 124 has been returned to a fully proximally retracted position (typically corresponding to a return to a jaws open configuration following a full closure and stapling cycle of the jaw assembly).

Thus, the "lock In" feature prevents a user from removing the shaft from the handle once the drive member 26 has been driven forward. Once the locking member 24 is situated in the slot or ledge of a rotation insert of the coupler 46, a release knob of the coupler 46 is unable to be pulled back. This locking action on the coupler prevents the user from rotating the shaft 20 out of the bayonet connection of the coupler 46 once actuation of the stapler has begun.

With reference to FIGS. 11, 12, and 13A-13F, an embodiment of articulation mechanism for the powered handle 40 is illustrated. In the illustrated embodiment, the handle can articulate the jaw assembly at the distal end of the shaft up to 45° in a fully articulated position in either direction relative to a longitudinally centered position. In some embodiments, the powered handle uses a manual articulation mechanism including a series of components coupled to the manually actuated articulation knob 190 at the proximal end of the handle. In other embodiments, the manually actuated articulation knob and certain associated elements of the articulation mechanism can be positioned in other locations on the handle such as adjacent a distal end of the handle.

Figure 11:
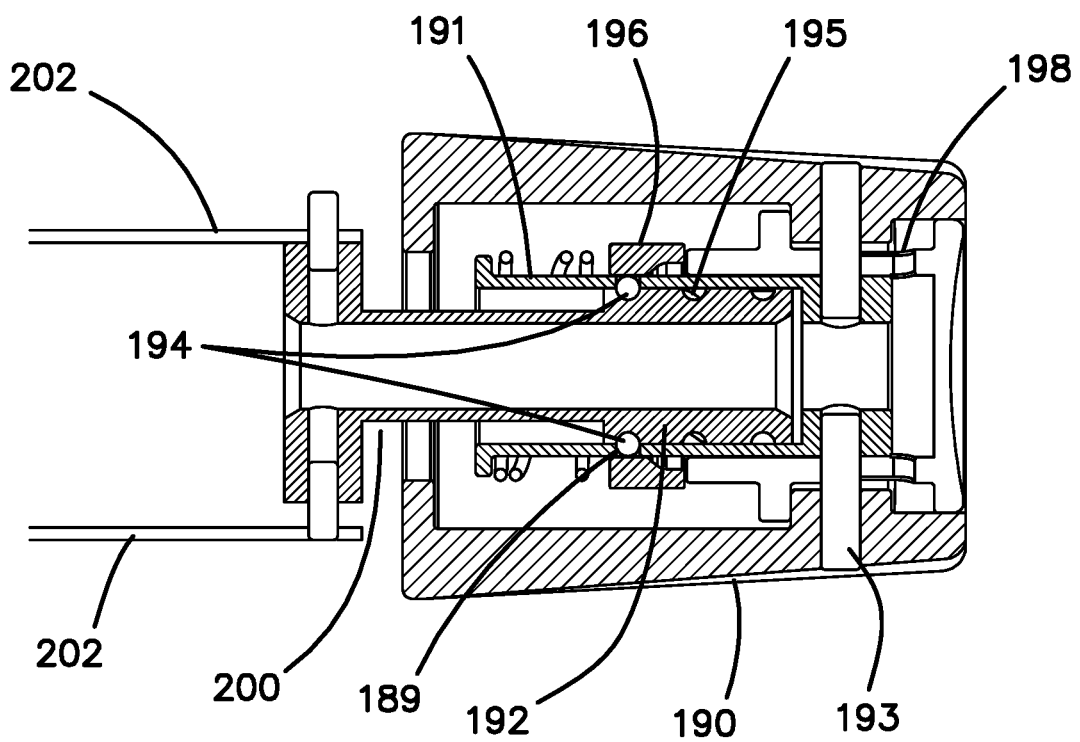
FIG. 11 is a cut-away side view of an embodiment of articulation mechanism of the powered handle of FIG. 2.
Figure 12:
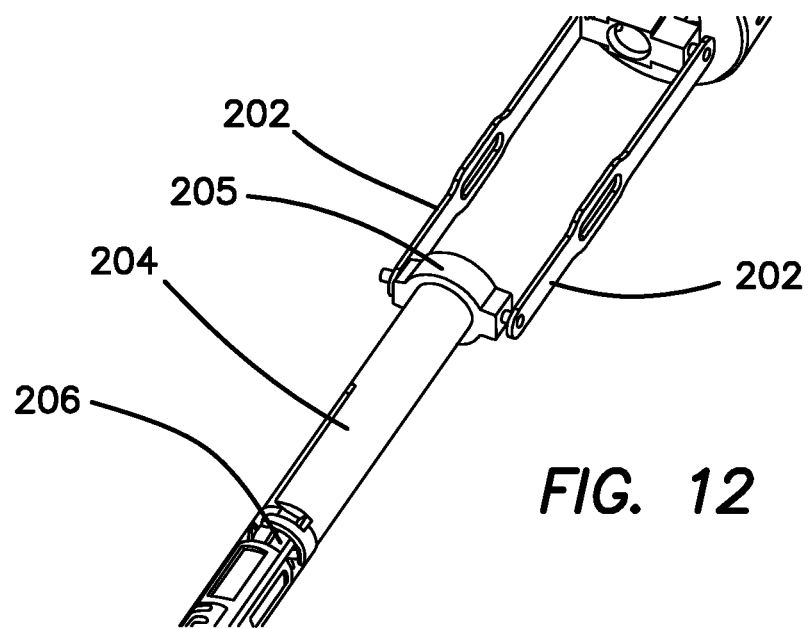
FIG. 12 is a perspective view of the articulation mechanism of FIG. 11 in an articulated position.

With reference to FIGS. 11 and 12, the articulation mechanism is coupled to an articulation member 206 extending longitudinally within the reload shaft when the reload shaft is coupled to the handle. Actuation of the articulation mechanism longitudinally translates the articulation member 206 proximally or distally relative to the shaft to articulate the jaw assembly at the distal end of the shaft.

With reference to FIG. 11, the articulation mechanism comprises a ball screw 192 having at least one helical groove or thread 195 in which one or more ball bearing 194 can ride. In the illustrated embodiment, the articulation mechanism comprises two ball bearings 194 that are engageable in two threads 195. The ball bearings 194 are positioned in ball bearing apertures 189 in a ball sleeve 191 positioned radially outwardly of the ball screw 192. The ball bearings 194 are maintained in the threads 195 by a release sleeve 196 positioned radially outward of the ball bearings 194. Rotation of the articulation knob 190, which is coupled to the ball sleeve 191 such as by connecting pins 193, rotates the ball sleeve 191 about an axis of rotation, causing the ball bearings 194 to travel within the threads 195 and correspondingly longitudinally translate the ball screw 192. Articulation of the jaw assembly is accomplished by rotating the articulation knob 190 to correspondingly rotate the ball sleeve 191 and the ball bearings 194 about the axis of rotation while their longitudinal position is fixed along the axis of rotation. The ball bearings 194, which are engaged in the threads 195 of the ball screw 192 will then translate the ball screw 192 forward and reverse along the axis of rotation. In the illustrated embodiment, the ball sleeve 191 is generally tubular, having a cavity formed therein, and a portion of the ball screw 192 is positioned within the cavity and translates longitudinally within the cavity. While the illustrated embodiment of articulation mechanism includes two ball bearings engageable threads in a ball screw, it is contemplated that in other embodiments, the articulation mechanism can have fewer or more than two ball bearings such as, for example, a single ball bearing positioned in a single helical screw or three or more ball bearings in a corresponding number of helical threads.

With reference to FIGS. 11 and 12, the ball screw 192 extends to a distal end 200 coupled to a pair of articulation links 202. The articulation links 202 are spaced apart from one another, which desirably allows them to be positioned radially outwardly of the drive system and actuation shaft within the handle. As illustrated in FIG. 12, the articulation links 202 can comprise a mating feature such as a slot formed therein to allow them to be keyed into a corresponding mating feature such as a post extending radially inwardly from the handle body. The slots can stabilize the articulation links relative to the handle and interaction of the handle posts with ends of the slots can define a range of articulation for the articulation mechanism. The distal ends of the articulation links 202 can be rotatably coupled to the articulation adapter 204, which can be positioned coaxially radially outwardly of the actuation adapter at the distal end of the handle. This rotational coupling can include an articulation bearing 205 having relatively low friction properties. This articulation bearing 205 can facilitate rotation of a coupled reload shaft relative to the handle assembly and longitudinal movement of the articulation adapter 204 during operation of the articulation mechanism. While the illustrated embodiment of articulation mechanism includes two articulation links laterally offset from the actuation mechanism within the handle, it is contemplated that in other embodiments, the articulation mechanism can have fewer or more than two articulation links such as, for example, an articulation link or three or more articulation links.

With continued reference to FIG. 12, the articulation adapter 204 can be connected to the articulation member 206 in the shaft by a bayonet connection when the shaft is coupled to the handle. The threads 195 can be configured such that moving the ball screw proximally will articulate the jaw assembly to the left when viewed from the handle relative to a longitudinally centered position and moving the ball screw 192 distally will articulate the jaw assembly to the right when viewed from the handle relative to the centered position.

Advantageously, since the helical threads 195 of the ball screw 192 are continuous, the articulation mechanism can allow the jaw assembly to be articulated to virtually infinite angular positions between a desired operational range. In some embodiments, the articulation mechanism can be configured to provide an articulation operational range from −45° to +45° of the jaw assembly relative to a longitudinally centered position defined by the longitudinal axis of the shaft. In other embodiments, the articulation mechanism can be configured to provide other operative articulation ranges including ranges providing more than +/−45° of articulation or those providing less than +/−45° of articulation. In some embodiments, the articulation mechanism can be configured to provide articulation in a single direction relative to a longitudinally centered position.

In some embodiments, the pitch of the threads 195 on the ball screw 192 is variable. For example, the threads 195 can include a relatively low pitch towards an end of the threads to advantageously provide a larger mechanical advantage when the jaw assembly can require more force to articulate. The threads 195 can include a relatively higher pitch towards a center of the threads to allow rapid movement with a relatively lower mechanical advantage where the jaw assembly can require a lower force to articulate. In other embodiments, the threads 195 include a constant pitch such that rotation of the articulation knob results in a proportional amount of articulation of a jaw assembly of the stapler that does not vary over the articulation range of the articulation mechanism. Desirably, such a constant pitch thread ball screw can result in an easily predictable response during operation of the actuation mechanism.

With reference to FIGS. 13A-13F, the articulation mechanism can comprise a release mechanism that allows the articulation mechanism to advantageously be reset to the longitudinally centered position from any articulated position. The release mechanism is operated by user pressing a release button 198. In the illustrated embodiment, the release button 198 is positioned radially nested within the articulation knob 190.

Figure 13A:
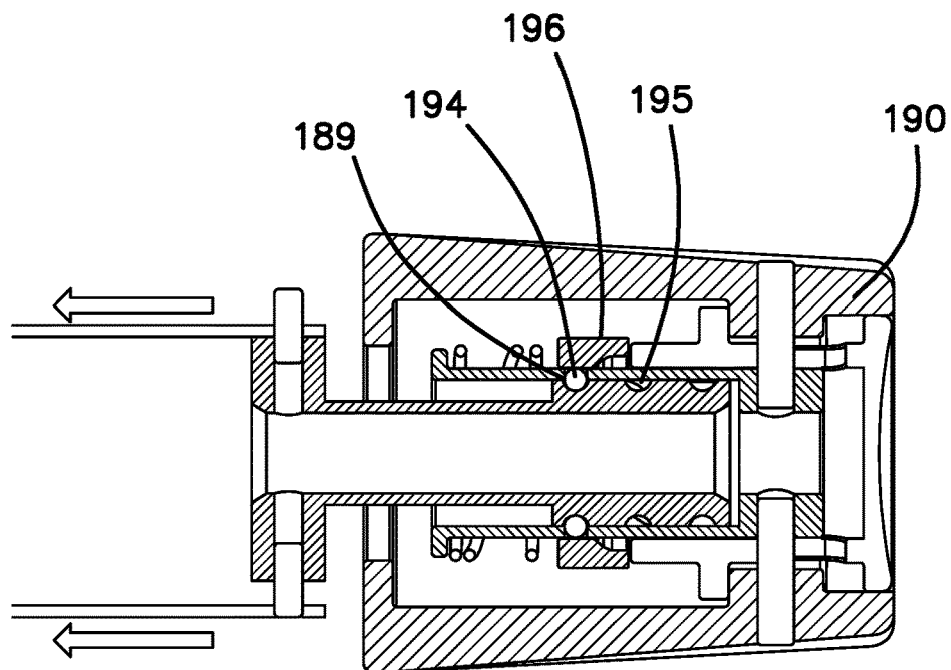
FIG. 13A is a cut-away side view of the articulation mechanism of FIG. 11.
Figure 13B:
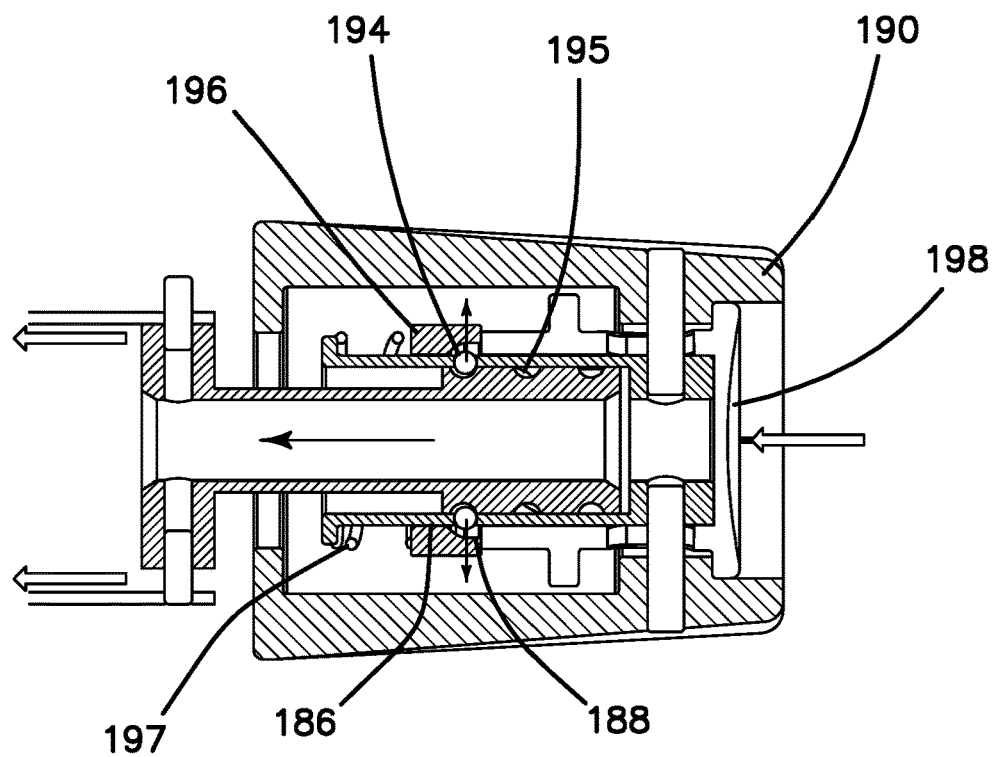
FIG. 13B is a cut-away side view of the articulation mechanism of FIG. 11 with a release button depressed.

With reference to FIG. 13B, operation of the release button 198 will distally advance the release sleeve 196. A radially inner surface of the release sleeve 196 is stepped to include an engagement surface 186 having a relatively small inner diameter and a release surface 188 having a relatively larger inner diameter with a smooth ramp between the engagement surface and the release surface. In operation, the engagement surface of the release sleeve maintains the ball bearings 194 in the threads 195 of the ball screw 192. Once the release button 198 is pushed, the engagement surface is distally advanced, allowing the ball bearings 194 to disengage from the threads 195 and advance radially outward through the ball bearing apertures 189 in the ball sleeve against the release surface.

Figure 13C:
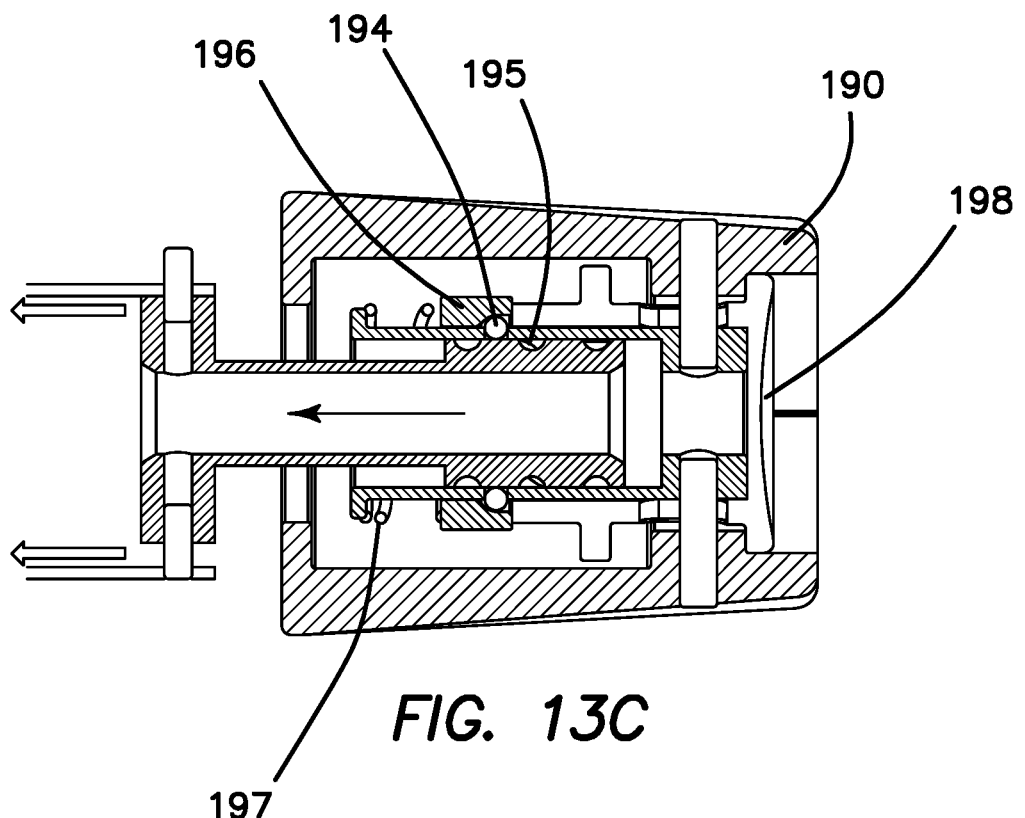
FIG. 13C is a cut-away side view of the articulation mechanism of FIG. 11 with the release button depressed and partially returned to a centered position.
Figure 13D:
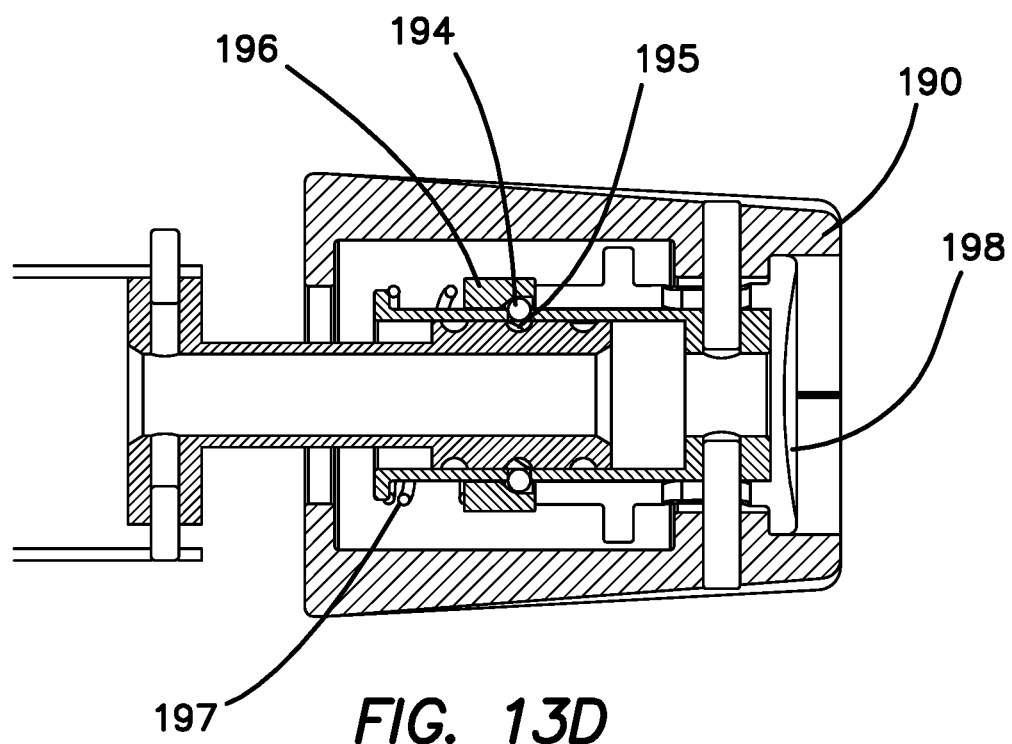
FIG. 13D is a cut-away side view of the articulation mechanism of FIG. 11 with the release button depressed and returned to a centered position.

With reference to FIGS. 13C and 13D, with the ball bearings 194 disengaged from the threads 195, the articulation mechanism can be biased to a centered position. In some embodiments, the ball screw 192 is biased to a centered position by a biasing member such as two springs 197 and spring force from the shaft. The ball bearings 194 positioned in the centered position (FIG. 13D) along the threads 195 corresponds to a longitudinally centered position of the jaw assembly.

Figure 13E:
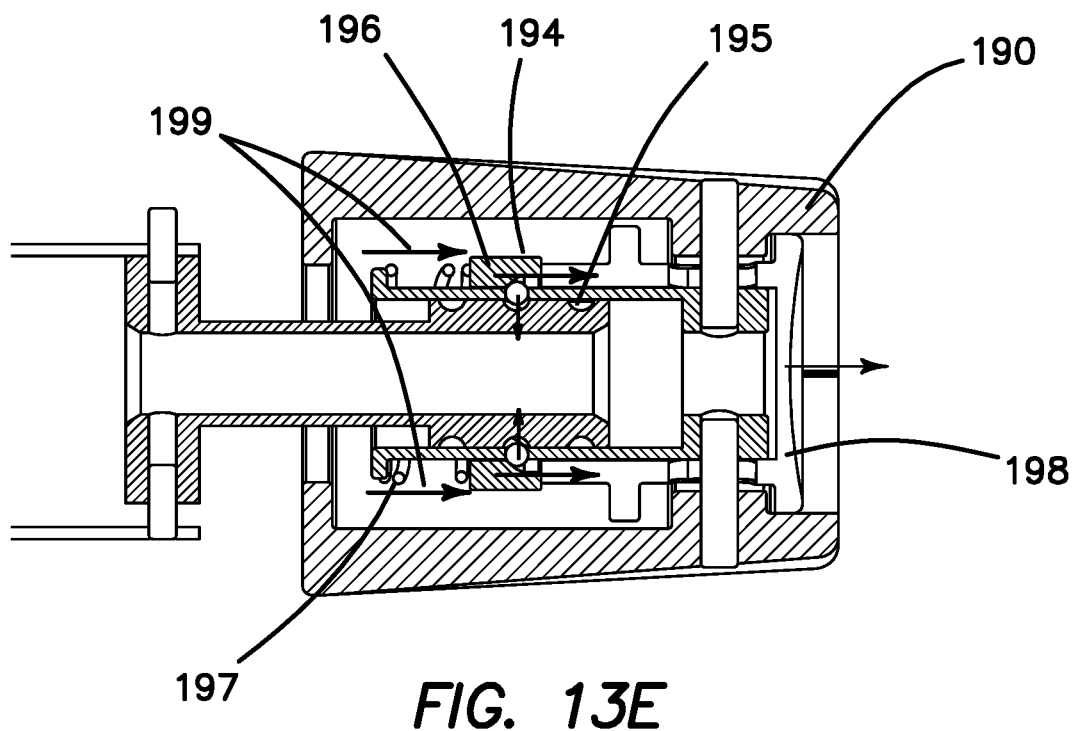
FIG. 13E is a cut-away side view of the articulation mechanism of FIG. 11 in the centered position with the release button partially released.
Figure 13F:
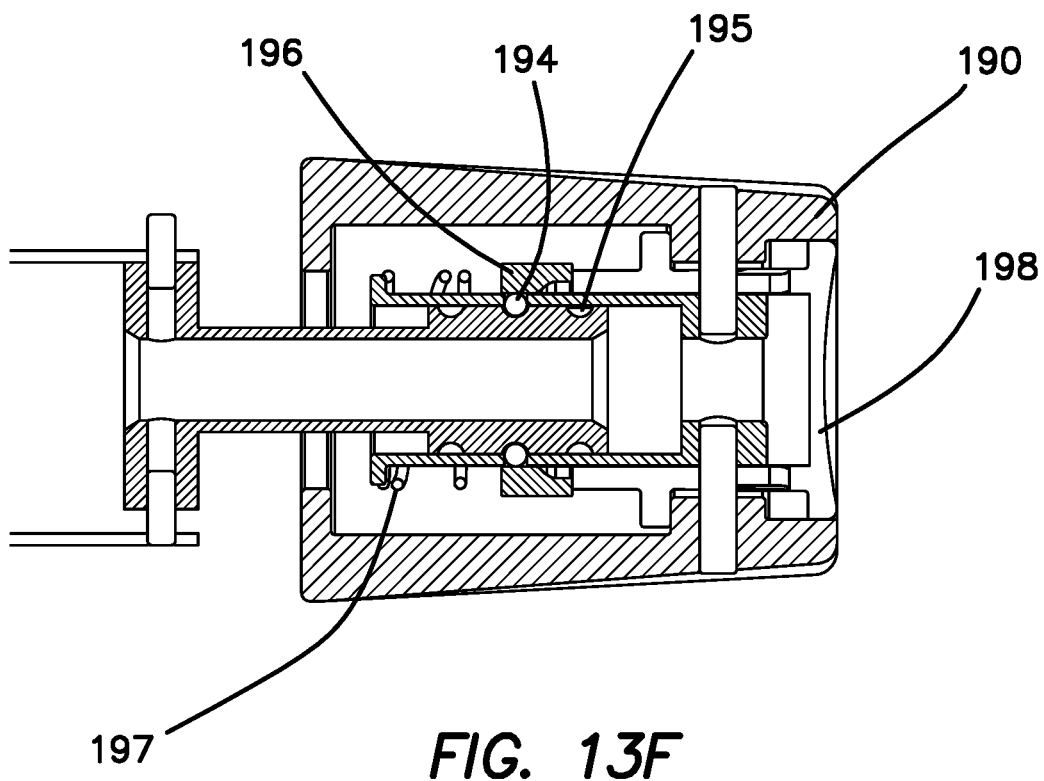
FIG. 13F is a cut-away side view of the articulation mechanism of FIG. 11 in the centered position.

With reference to FIGS. 13E-13F, once the release button 198 is allowed to return to an undisturbed configuration, release sleeve 196 is retracted proximally (indicated by arrows 199) by a spring. Proximal movement of the release spring 196 forces the ball bearings 194 into engagement with the threads 195 of the ball screw. Thus, the articulation mechanism can then be used to articulate the jaw assembly from the longitudinally centered position, or the stapler can be used with the jaw assembly in the longitudinally centered position.

With reference to FIGS. 14, 15, and 16A-16B, an embodiment of manual return mechanism for the powered handle is illustrated. A manual return mechanism can advantageously provide a redundant return mechanism in the event of a power supply failure, other powered component failure, or mechanical failure or binding.

Figure 14:
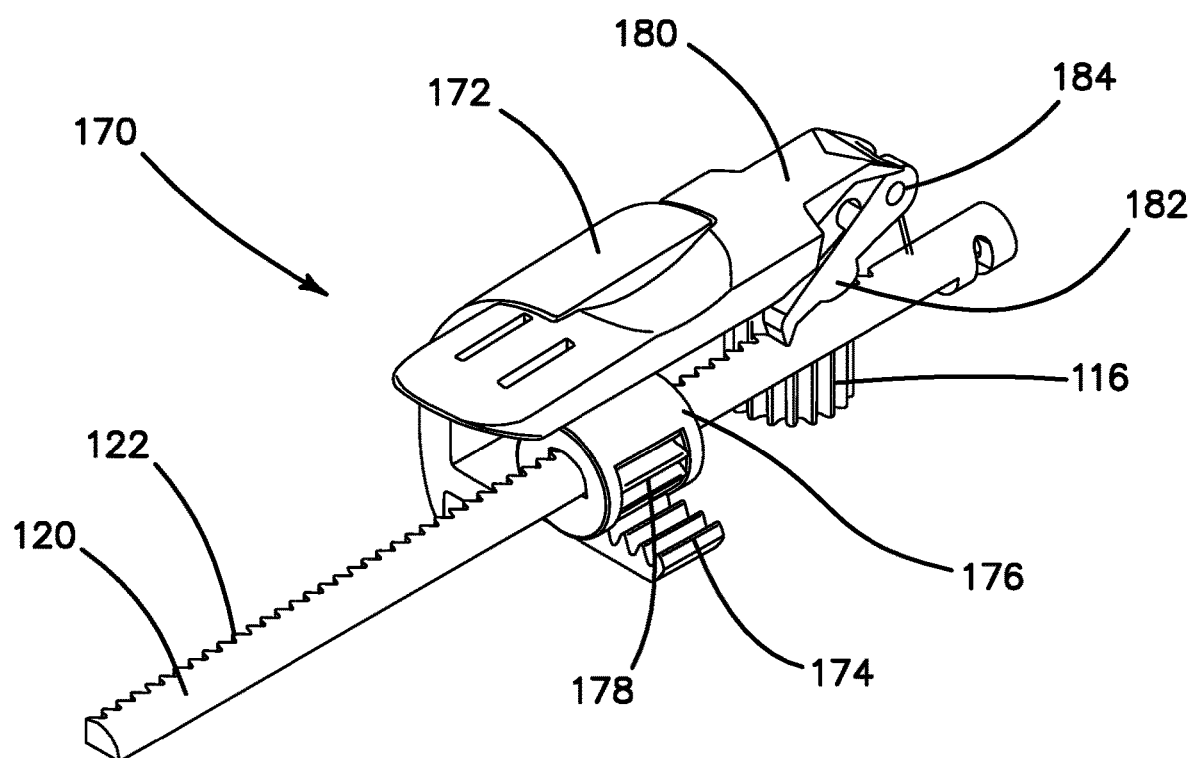
FIG. 14 is a perspective view of an embodiment of manual return assembly for the powered handle of FIG. 2.
Figure 15:
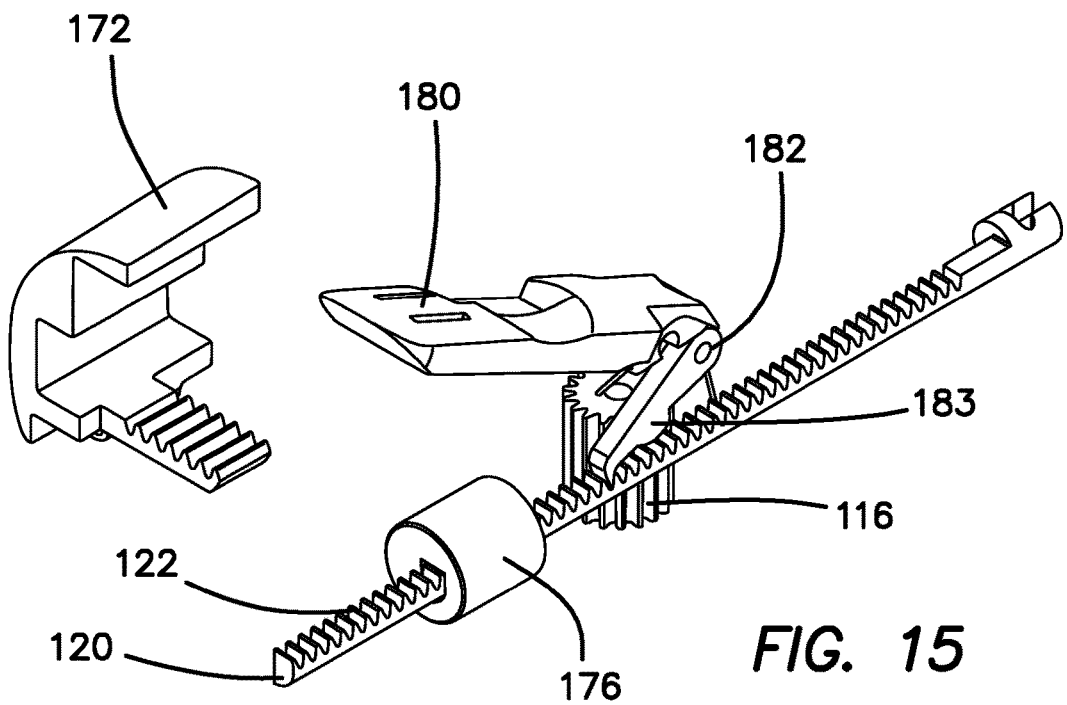
FIG. 15 is a perspective view of the manual return assembly of FIG. 14 with a decoupling mechanism actuated.

With reference to FIGS. 14 and 15, the manual return mechanism includes two separate, independently operable subassemblies that are operated in sequence to return the actuation shaft 120 to a proximal-most position within the handle, which corresponds to the open configuration of the jaw assembly. As illustrated, the manual return mechanism 170 comprises a shaft rotation mechanism and a shaft retraction mechanism. In operation, when it is desirable to manually return the stapler to the open configuration, the shaft rotation mechanism is initially operated.

With reference to FIGS. 14 and 15, to operate the shaft rotation mechanism of the manual return mechanism 170, a user pulls a disengagement tab 172 positioned on an outer surface of the handle. The disengagement tab 172 has a disengagement rack 174 formed thereon. The disengagement rack 174 is in meshed engagement with a shaft rotation rack 176 formed on a shaft rotation collar 176. The actuation shaft 120 extends through the shaft rotation collar 176 and is slideable therethrough. Thus pulling the disengagement tab 172 rotates the actuation shaft 120 approximately 90 degrees about the longitudinal axis thereof. This rotation positions the rack 122 of the actuation shaft out of engagement with the auxiliary gear 116 of the drive system. Moreover, in some embodiments, removal of the disengagement tab 172 from the handle can also disengage the power supply from the drive system or otherwise disengage the control system to prevent further powered operation of the powered handle. Additionally, the shaft rotation mechanism can be configured to be operated a single time only. For example, in the illustrated embodiment a return pawl 182 on the shaft retraction mechanism can comprise an interference lobe 183 sized and configured to interfere with the drive system to prevent closure of the return lever and rotation of the actuation shaft 120 back into engagement with the auxiliary gear once the shaft rotation disengagement tab 172 has been pulled. Thus, once the shaft rotation mechanism has been operated, the handle can be disabled from further use.

Figure 16A:
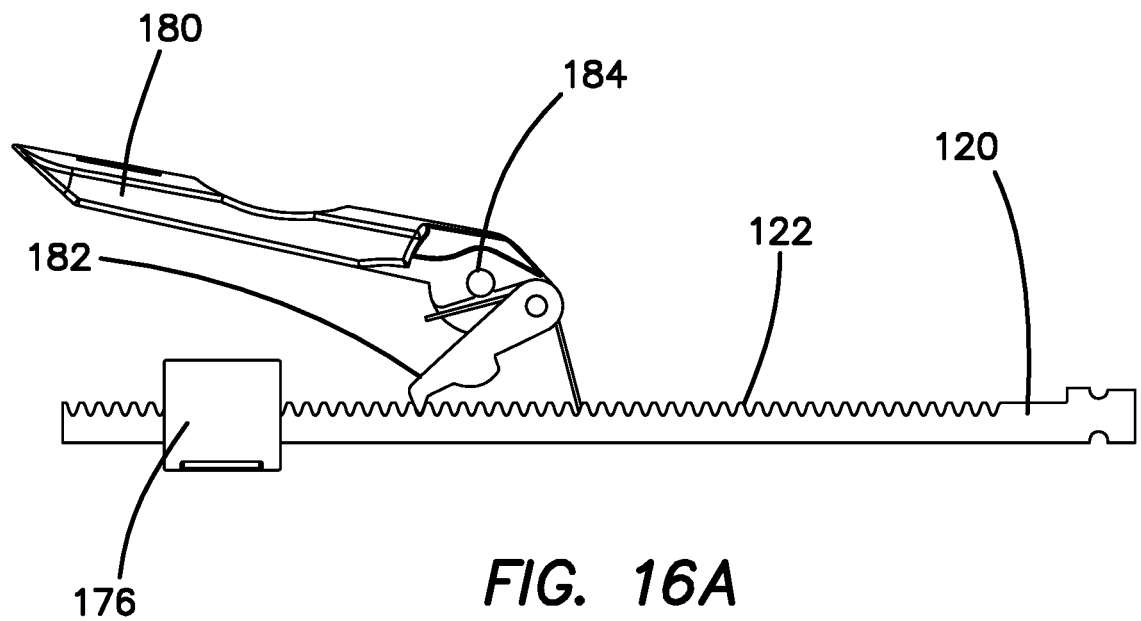
FIG. 16A is a side view of the manual return assembly of FIG. 14 with a return mechanism partially actuated.
Figure 16B:
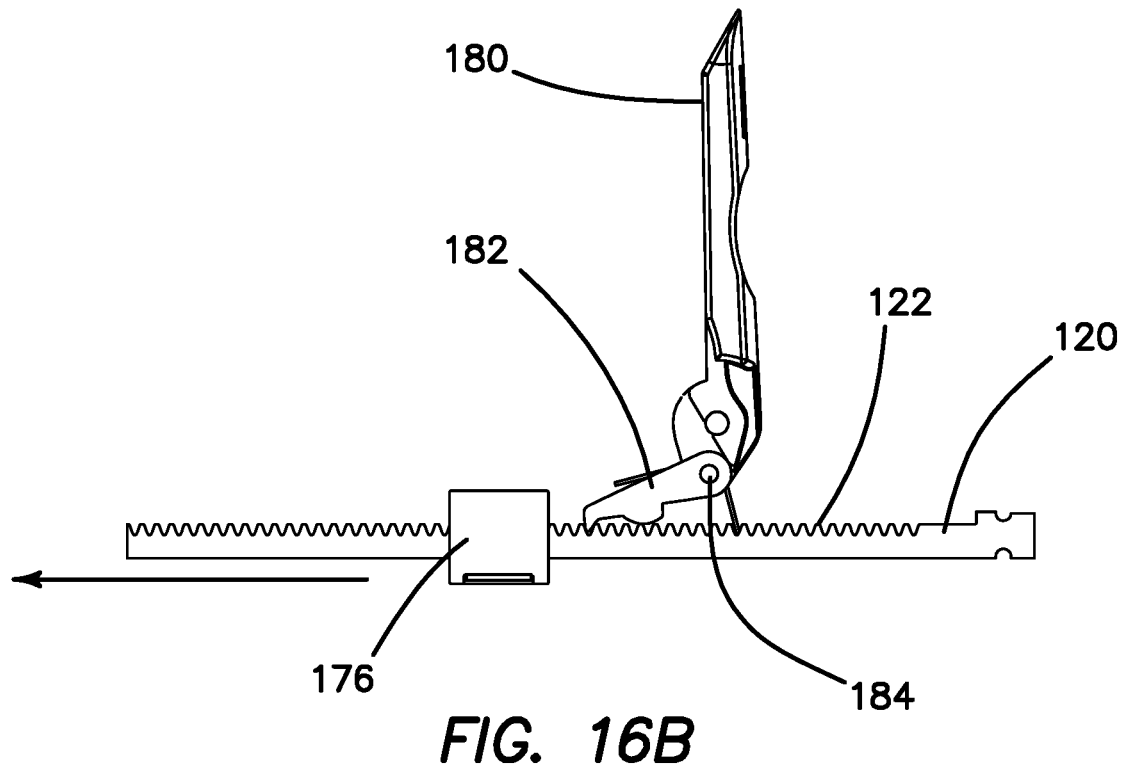
FIG. 16B is a side view of the manual return assembly of FIG. 14 with the return mechanism actuated through a full return stroke.
Figure 17:
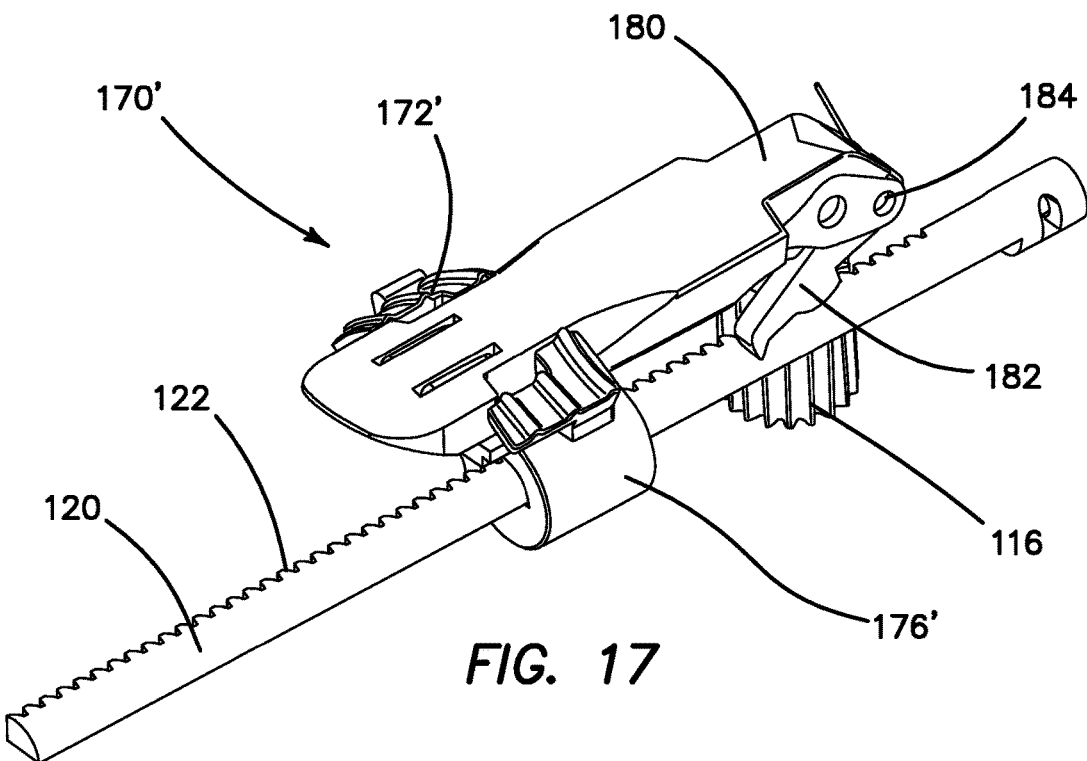
FIG. 17 is a perspective view of an embodiment of manual return assembly for the powered handle of FIG. 2.
Figure 18:
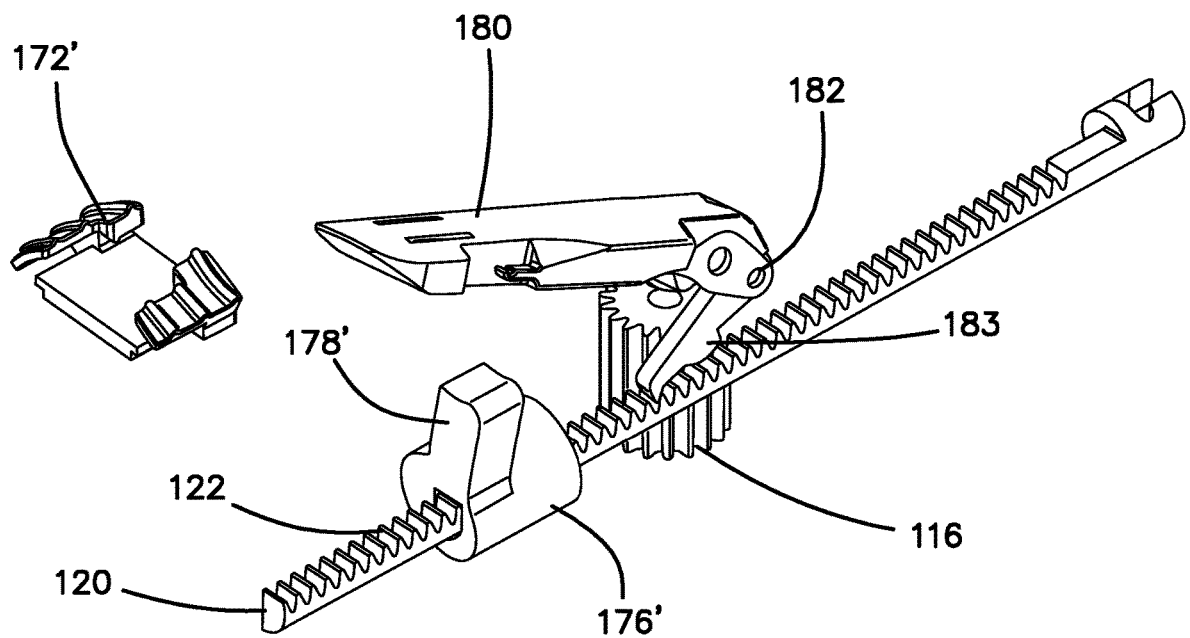
FIG. 18 is a perspective view of the manual return assembly of FIG. 17 with a decoupling mechanism actuated.
Figure 19A:
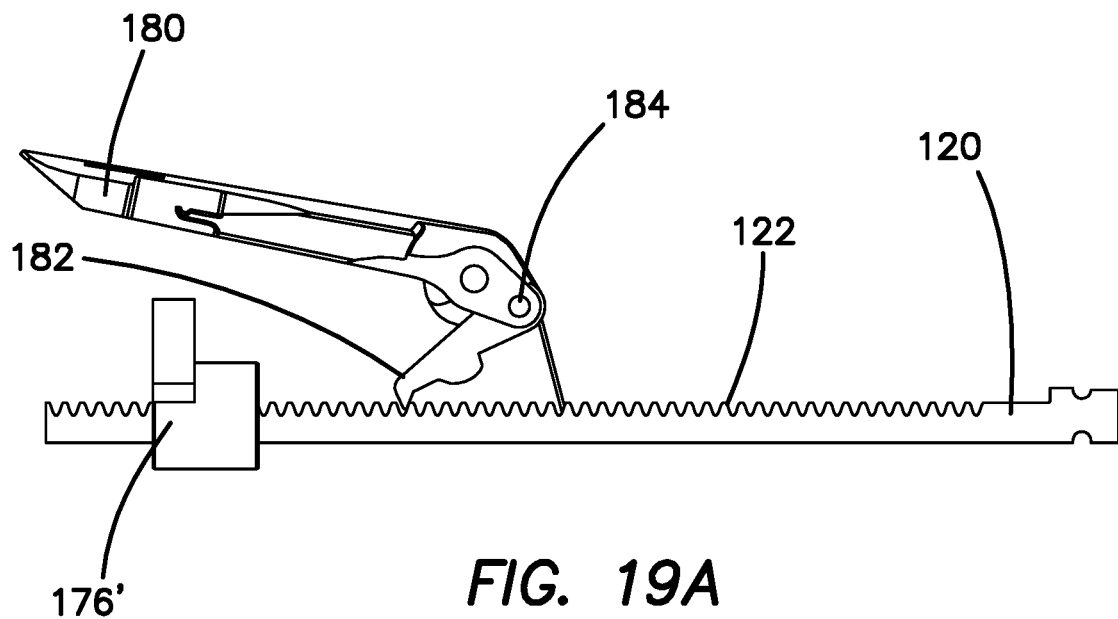
FIG. 19A is a side view of the manual return assembly of FIG. 17 with a return mechanism partially actuated.
Figure 19B:
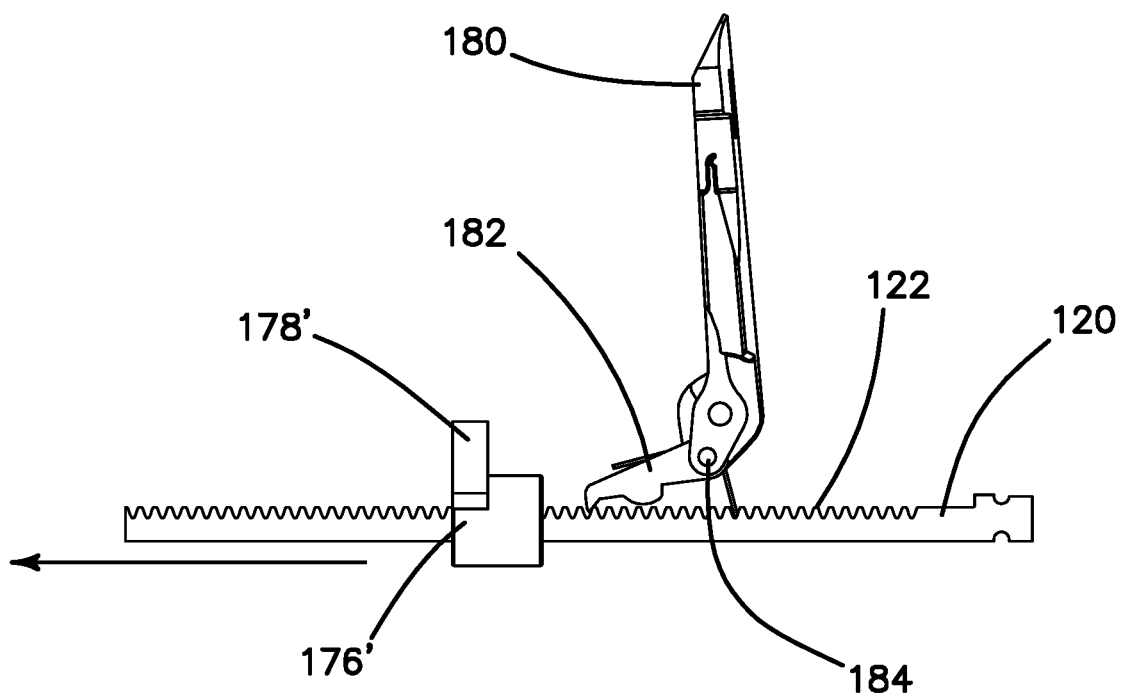
FIG. 19B is a side view of the manual return assembly of FIG. 17 with the return mechanism actuated through a full return stroke.

With reference to FIGS. 15 and 16A-16B, once the shaft rotation mechanism has been operated, the shaft retraction mechanism can be operated to return the actuation shaft proximally within the handle. Removal of the disengagement tab 172 from the handle exposes a return lever 180 on the powered handle. The return lever 180 is pivotably coupled to a return pawl 182 at a pivot joint 184. When the rack 122 of the actuation shaft 120 was rotated out of engagement with the drive system, it was rotated into engagement with the shaft retraction mechanism. The return lever 180 can be rotated through one or a series of return cycles (FIGS. 16A, 16B) to engage the return pawl 182 with the rack 122 on the actuation shaft 120 and retract the actuation shaft 120 proximally within the handle in a ratchet-type operation.

With reference to FIGS. 17, 18, and 19A-19B, another embodiment of manual return mechanism for the powered handle is illustrated. The components and operation of the manual return mechanism 170' are similar to that described above with respect to the manual return mechanism 170 of FIGS. 14, 15, and 16A-16B. However, in use of the manual return mechanism 170', removal of a disengagement tab 172' from the handle assembly exposes a shaft rotation collar 176' having a rotation lever 178' protruding therefrom. With the handle assembly in powered operation, the disengagement tab 172' covers the shaft rotation collar 176' on an outer surface of the handle. Once the disengagement tab has been removed, a user can then manipulate the rotation lever 178' to rotate the actuation shaft 120 such that the shaft retraction mechanism can be operated to return the actuation shaft proximally within the handle. The shaft retraction mechanism of the manual return mechanism 170' includes the same ratchet-type operation as that discussed above with respect to the manual return mechanism 170. Desirably, in some handle configurations, the rotation lever 178' can provide enhanced mechanical advantage to facilitate rotation of the actuation shaft as compared to the shaft rotation mechanism including a disengagement rack 174 of FIGS. 15, 15, and 16A-16B.

Although this application discloses certain preferred embodiments and examples, it will be understood by those skilled in the art that the present inventions extend beyond the specifically disclosed embodiments to other alternative embodiments and/or uses of the invention and obvious modifications and equivalents thereof. Further, the various features of these inventions can be used alone, or in combination with other features of these inventions other than as expressly described above. Thus, it is intended that the scope of the present inventions herein disclosed should not be limited by the particular disclosed embodiments described above, but should be determined only by a fair reading of the claims.

What is claimed is:

1. A handle assembly for a surgical stapler, the handle assembly comprising:
    a handle body comprising a stationary handle and a trigger pivotably coupled to the handle body;
    an electric motor disposed within the handle body, the motor comprising an output shaft;
    an actuation shaft slidable within the handle body along a longitudinal axis;
    a motor gear coupled to the output shaft of the motor;

an auxiliary gear in driven engagement with the motor gear and operatively engaged with the actuation shaft;
a crown gear mounted in the handle in meshed engagement with the motor gear;
a potentiometer coupled to the crown gear; and
a control system electrically coupled to the trigger, the electric motor, and the potentiometer, the control system configured to control the speed and torque of the electric motor.

2. The handle assembly of claim 1, wherein the control system is configured to measure a longitudinal position of the actuation shaft.

3. The handle assembly of claim 2, wherein the control system measures changes of resistance at the potentiometer to determine a position of the actuation shaft.

4. The handle assembly of claim 1, further comprising a circuit board, and wherein the potentiometer and the control system are mounted on the circuit board.

5. The handle assembly of claim 1, wherein the actuation shaft comprises a rack extending longitudinally thereon and wherein the auxiliary gear is in meshed engagement with the rack.

6. The handle assembly of claim 5, further comprising a guide member through which the actuation shaft slides, and wherein the auxiliary gear is supported in the guide member.

7. The handle assembly of claim 1, further comprising a manual return system selectively operable to disengage the auxiliary gear from the actuation shaft and return the actuation shaft proximally within the handle body.

8. The handle assembly of claim 1, further comprising a manual articulation mechanism.

9. The handle assembly of claim 8, wherein the manual articulation mechanism comprises a manually actuated articulation knob positioned at a proximal end of the handle body and rotatable about the longitudinal axis; and a ball screw operatively coupled to the articulation knob and longitudinally movable by rotation of the articulation knob.

10. A handle assembly for a surgical stapler, the handle assembly comprising:
a handle body comprising a stationary handle and a trigger pivotably coupled to the handle body;
an electric motor disposed within the handle body, the motor comprising an output shaft;
an actuation shaft slidable within the handle body along a longitudinal axis;
a motor gear coupled to the output shaft of the motor;
an auxiliary gear in driven engagement with the motor gear and operatively engaged with the actuation shaft;
a position sensor operably coupled to the motor gear to determine a longitudinal position of the actuation shaft;
a control system electrically coupled to the trigger, the electric motor, and the position sensor, the control system configured to control the speed and torque of the electric motor; and
a manual return mechanism selectively operable to disengage the auxiliary gear from the actuation shaft and retract the actuation shaft proximally.

11. The handle assembly of claim 10, wherein the actuation shaft is rotatable about the longitudinal axis by the manual return mechanism from a first orientation in which the auxiliary gear is operatively engaged with the actuation shaft to a second orientation in which the auxiliary gear is disengaged from the actuation shaft.

12. The handle assembly of claim 10, wherein the position sensor comprises a potentiometer.

13. A handle assembly for a surgical stapler, the handle assembly comprising:
a handle body comprising a stationary handle and a trigger pivotably coupled to the handle body;
a powered drive system disposed within the handle body;
an actuation shaft slidable within the handle body along a longitudinal axis by actuation of the drive system;
a position sensor operably coupled to the motor gear to determine a longitudinal position of the actuation shaft;
a control system electrically coupled to the trigger, the drive system, and the position sensor;
a manual return mechanism selectively operable to disengage the drive system from the actuation shaft and retract the actuation shaft proximally; and
a manual articulation mechanism.

14. The handle assembly of claim 13, wherein the manual articulation mechanism comprises a manually actuated articulation knob positioned at a proximal end of the handle body and rotatable about the longitudinal axis; and a ball screw operatively coupled to the articulation knob and longitudinally movable by rotation of the articulation knob.

15. The handle assembly of claim 13, wherein the manual return mechanism comprises a shaft rotation mechanism configured to rotate the actuation shaft about the longitudinal axis from a first orientation in which the drive system is operatively engaged with the actuation shaft to a second orientation in which the drive system is disengaged from the actuation shaft.

\* \* \* \* \*